United States Patent
Sirois et al.

(10) Patent No.: US 11,707,233 B1
(45) Date of Patent: Jul. 25, 2023

(54) SIMULTANEOUS SUB-NYQUIST ACQUISITION OF A PLURALITY OF BIOELECTRIC SIGNALS

(71) Applicant: Wisear, Auxerre (FR)

(72) Inventors: Alain Sirois, Paris (FR); Claire Ben Ali, Paris (FR)

(73) Assignee: Wisear, Auxerre (FR)

( * ) Notice: Subject to any disclaimer, the term of this patent is extended or adjusted under 35 U.S.C. 154(b) by 0 days.

(21) Appl. No.: 18/082,598

(22) Filed: Dec. 16, 2022

(51) Int. Cl.
*A61B 5/00* (2006.01)
*A61B 5/389* (2021.01)

(52) U.S. Cl.
CPC ............ *A61B 5/7225* (2013.01); *A61B 5/389* (2021.01); *A61B 5/6803* (2013.01)

(58) Field of Classification Search
CPC ..... A61B 5/7225; A61B 5/389; A61B 5/6803; A61B 5/72–5/7296
See application file for complete search history.

(56) References Cited

U.S. PATENT DOCUMENTS

| 5,058,107 | A | * | 10/1991 | Stone | H04J 1/05 455/189.1 |
|---|---|---|---|---|---|
| 5,259,387 | A | | 11/1993 | DePinto | |
| 6,317,625 | B1 | | 11/2001 | Olson et al. | |
| 2011/0301439 | A1 | | 12/2011 | Albert et al. | |
| 2022/0299653 | A1 | * | 9/2022 | Morales | G01S 5/0221 |

FOREIGN PATENT DOCUMENTS

| CN | 203153725 U | 8/2013 |
|---|---|---|
| CN | 110101385 A | 8/2019 |
| CN | 109901711 B | 6/2020 |
| EP | 3643228 A1 | 4/2020 |
| KR | 101856781 B1 | 5/2018 |

OTHER PUBLICATIONS

Dennis M. Akos et. al, Direct Bandpass Sampling of Multiple Distinct RF Signals, Jul. 1999, pp. 983-988, vol. 47, No. 7, IEEE Transactions on communications.

(Continued)

*Primary Examiner* — Jonathan T Kuo
(74) *Attorney, Agent, or Firm* — Daylight Law, P.C.

(57) ABSTRACT

Methods and systems for simultaneous sub-Nyquist measurement of a plurality of bioelectric signals are disclosed. A system includes measurement and reference electrodes configured to measure a first and a second bioelectric signal simultaneously. The first signal is within a first frequency band, the second signal is within a second frequency band, the second band is higher than the first band, and the first and second bands are separated by a frequency gap. The system also includes a filter for attenuating in the frequency gap and a sampler configured to sample, by conducting a sampling at a sampling frequency, the first and second bioelectric signals as measured simultaneously by the measurement and reference electrodes. The sampling frequency is lower than the Nyquist frequency for the second signal. An alias of the second signal caused by the sampling is in the frequency gap. The alias does not overlap the first band.

30 Claims, 18 Drawing Sheets

(56) References Cited

OTHER PUBLICATIONS

G. Huang, N. Fu and L. Qiao, "Optimization Model Based Sub-Nyquist Sampling of Pulses With Various Shapes and Its Application to ECG Signals," in IEEE Access, vol. 6, pp. 62458-62469, 2018, doi: 10.1109/ACCESS.2018.2876393.

I.I Goncharova, D.J McFarland, T.M Vaughan, J.R Wolpaw, EMG contamination of EEG: spectral and topographical characteristics, Clinical Neurophysiology,vol. 114, Issue 9, 2003,pp. 1580-1593, ISSN 1388-2457.

Martinek, R.; Ladrova, M.; Sidikova, M.; Jaros, R.; Behbehani, K.; Kahankova, R.; Kawala-Sterniuk, A. Advanced Bioelectrical Signal Processing Methods: Past, Present, and Future Approach—Part III: Other Biosignals. Sensors 2021, 21, 6064.

Muthukumaraswamy SD. High-frequency brain activity and muscle artifacts in MEG/EEG: a review and recommendations. Front Hum Neurosci. 2013;7:138. Published Apr. 15, 2013.

\* cited by examiner

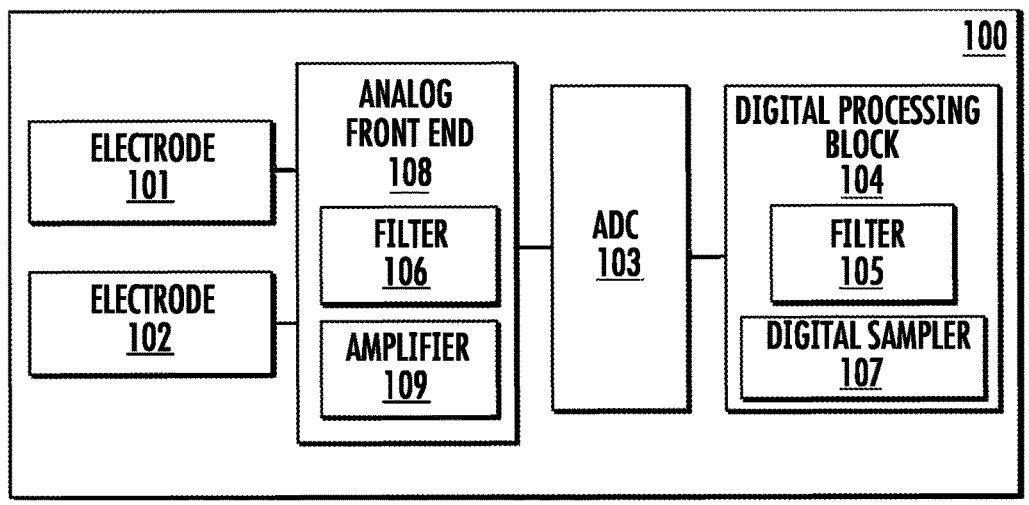
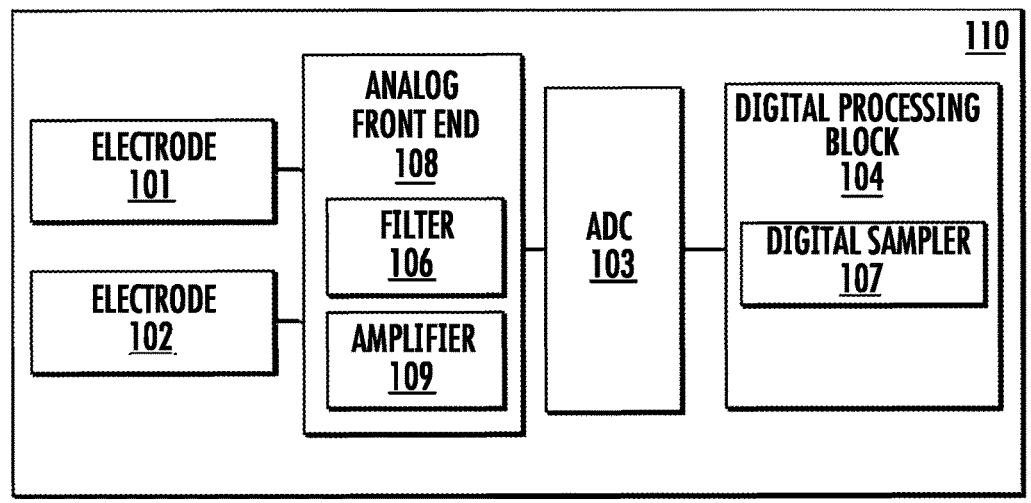
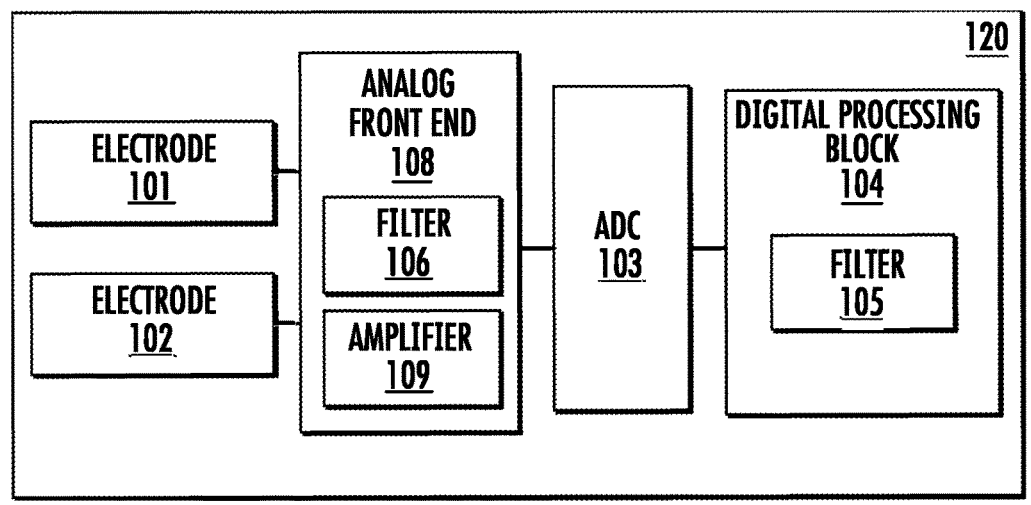
FIG. 1

SIMULTANEOUS SUB-NYQUIST ACQUISITION OF A PLURALITY OF BIOELECTRIC SIGNALS

BACKGROUND

Physical signals can be acquired for analysis by a computational system using an analog front end and an analog-to-digital converter (ADC) to digitize the signal. Digitizing a physical signal involves discretizing the signal across time by sampling the physical signal at a sampling frequency as well as rounding to the nearest discrete digital value allocated for the sampled signal value. The acquired digital signal is then a series of time samples of the physical signal spaced according to the sampling frequency and with each sample digitized according to the resolution of the sampling system. An accurate conversion of the physical signal into digital form is conducted using a sampling frequency that is sufficiently high to ensure that no information is lost due to an insufficient number of samples being taken.

The Nyquist-Shannon sampling theorem states that a signal must be sampled at a sampling frequency that is at least twice as high as the highest frequency component of the physical signal in order for the signal to be accurately acquired by the sampling processes without information loss. The criterion of this theorem is often referred to as the Nyquist criterion. If this criterion is not met, downstream computational systems may not have an accurate picture of the sampled signal because of aliasing—an effect that causes different signals to become indistinguishable after sampling because both the signals could generate the same set of samples even though they are different. The sampling frequency at which the physical signal must be acquired to meet the Nyquist criterion is referred to as the Nyquist frequency of the physical signal. The frequency band that extends from zero to half the Nyquist frequency is referred to as the first Nyquist zone. Throughout this disclosure, this sampling frequency can be referred to as the Nyquist frequency "associated with" a physical signal and the resulting Nyquist zone can be referred to as the Nyquist zone "associated with" the physical signal.

While a high sampling frequency tends to improve the fidelity of the digital acquisition of a signal, a high sampling frequency also puts pressure on the requirements of the analog front end and ADC. Furthermore, the high sampling frequency generates a larger number of data points for a given physical signal, and therefore increases the computational burden of conducting further analysis on the acquired physical signal. In certain applications in which the acquired physical signal is applied to complex computations, such as machine intelligence analyzers that are required to glean information from the physical signal in real time, the resulting increase in computational complexity caused by an increase in the number of data points on which those computations must be conducted can become a limiting economical factor in terms of the hardware requirements of the system, or may even render certain applications impracticable due to the required computational time relative to the speed at which outputs are required.

SUMMARY

Systems and methods directed to the simultaneous acquisition of a plurality of bioelectric signals are disclosed herein. The systems and methods disclosed herein involve sampling a plurality of bioelectric signals simultaneously at a sampling frequency which is below the Nyquist frequency of the highest frequency bioelectric signal in the plurality of bioelectric signals. The sampling of a signal below the Nyquist frequency for the signal is referred to herein as sub-Nyquist sampling and the acquisition of a digital signal using such sampling is referred to as sub-Nyquist acquisition. Furthermore, specific embodiments of the inventions disclosed herein can achieve simultaneous sub-Nyquist acquisition of a plurality of bioelectric signals without losing any of the information of the plurality of bioelectric signals that would otherwise have been lost due to sub-Nyquist sampling. Specific embodiments disclosed herein can achieve this effect through the intentional aliasing of one or more of the bioelectric signals in the plurality of bioelectric signals into one or more frequency gaps between the individual bioelectric signals in the plurality of bioelectric signals. Specific embodiments disclosed herein form the one or more frequency gaps by using one or more filters with specific characteristics and specific sub-Nyquist sampling frequencies which are determined according to the techniques described below.

Sub-Nyquist acquisition of a plurality of bioelectric signals provides significant benefits to the analysis of bioelectric signals because in specific applications, bioelectric signals must be analyzed across a fixed time window to distinguish specific biological occurrences with which the signals are associated. As such, decreasing the sampling frequency decreases the amount of data that must be analyzed in that fixed time window to achieve those results. This is important because when running signal processing and machine learning algorithms on such data series, the number of calculations is directly related to the number of data points in the data series. As such, decreasing the sampling frequency can lead to significant benefits. This is particularly important when the processing is being conducted with embedded systems using microcontrollers or systems on chips (SoCs) with limited computational resources. Regardless, in any application, reducing the sampling frequency can lead to a decrease in the storage requirements for the computational system (e.g., decrease in memory requirements such as random access memory (RAM) size), a decrease in processing resources (e.g., decrease in the number of operations a central processing unit (CPU) will need to conduct in a given time), a decrease in latency (e.g., less impact on user experience from signal acquisition to signal recognition and utilization), and a decrease in energy consumption (e.g., a lengthening of battery life for a mobile battery powered system).

In specific embodiments of the invention, a bioelectric signal acquisition system is provided. The bioelectric signal acquisition system comprises a measurement electrode and a reference electrode. The measurement electrode and the reference electrode are configured to measure a first bioelectric signal and a second bioelectric signal simultaneously. The first bioelectric signal is within a first frequency band. The second bioelectric signal is within a second frequency band. The second frequency band is higher than the first frequency band. The first frequency band and the second frequency band are separated by a frequency gap. The system also comprises a filter for attenuating in the frequency gap, and a sampler configured to sample, by conducting a sampling at a sampling frequency, the first bioelectric signal and the second bioelectric signal as measured simultaneously by the measurement electrode and the reference electrode. The sampling frequency is lower than the Nyquist frequency for the second bioelectric signal. An alias of the second bioelectric signal caused by the sampling is in the frequency gap. The alias does not overlap the first frequency band.

In specific embodiments of the invention, a method is provided. The method comprises measuring, using a measurement electrode and a reference electrode, a first bioelectric signal and a second bioelectric signal simultaneously. The first bioelectric signal is within a first frequency band. The second bioelectric signal is within a second frequency band. The second frequency band is higher than the first frequency band. The first frequency band and the second frequency band are separated by a frequency gap. The method also comprises attenuating, using a filter, in the frequency gap. The method also comprises sampling, using a sampler and by conducting a sampling at a sampling frequency, the first bioelectric signal and the second bioelectric signal as measured simultaneously by the measurement electrode and the reference electrode. The sampling frequency is lower than the Nyquist frequency for the second bioelectric signal, an alias of the second bioelectric signal caused by the sampling is in the frequency gap, and the alias does not overlap the first frequency band.

In specific embodiments of the invention, one or more non-transitory computer-readable media storing instructions that, when executed by one or more processors of a bioelectric signal acquisition system, cause the bioelectric signal acquisition system to conduct a method in accordance with the prior paragraph are provided.

BRIEF DESCRIPTION OF THE DRAWINGS

FIG. 1 illustrates block diagrams for various bioelectric signal acquisition systems in accordance with specific embodiments of the inventions disclosed herein.

DETAILED DESCRIPTION

Figure 2:
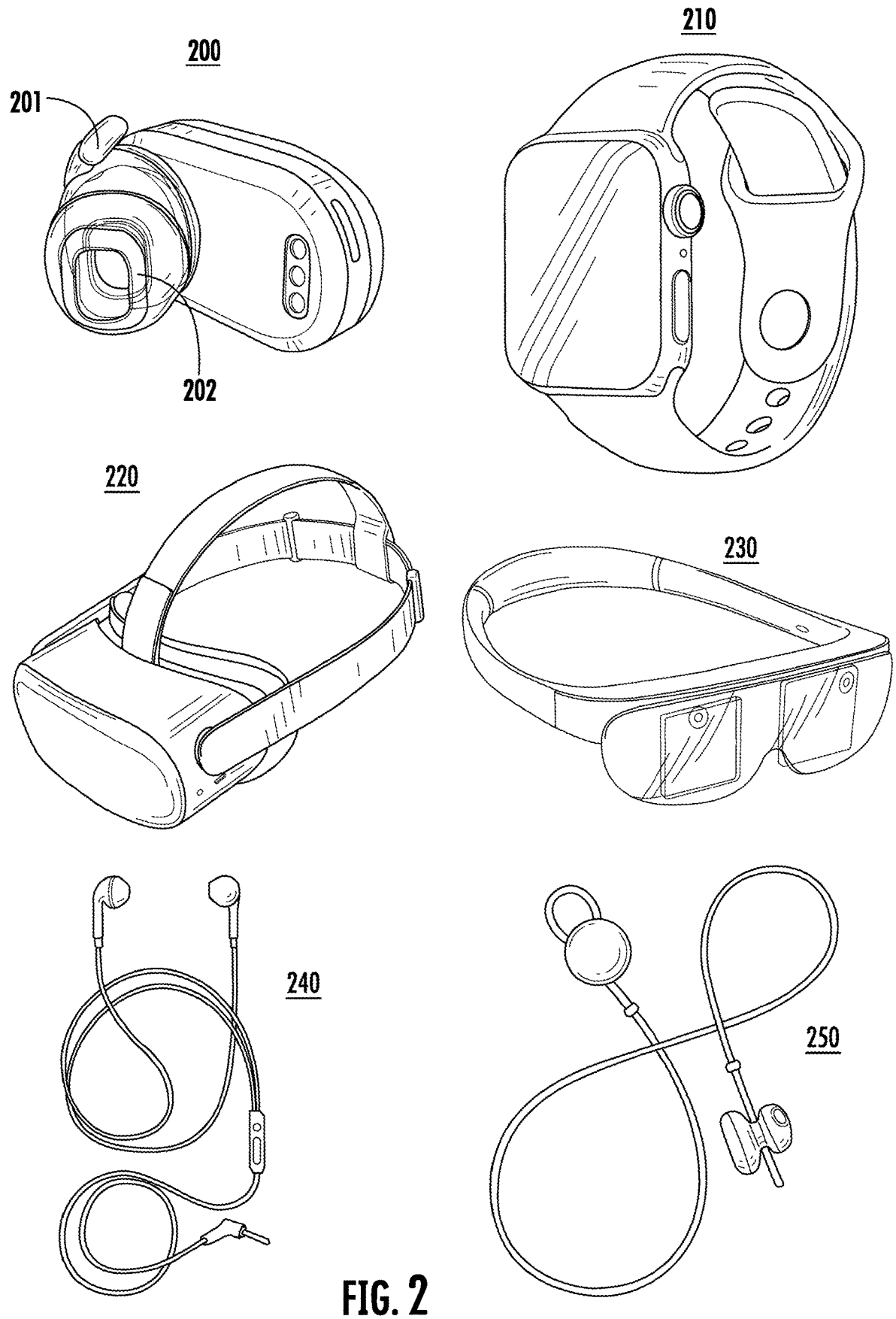
FIG. 2 illustrates various wearable devices that can form part of various bioelectric signal acquisition systems in accordance with specific embodiments of the inventions disclosed herein.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Different methods and systems for the simultaneous acquisition of bioelectric signals will be described in detail in this disclosure. The methods and systems disclosed in this section are non-limiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

Bioelectric signal acquisition systems in accordance with this disclosure can include various components for acquiring bioelectric signals. The bioelectric signal acquisition systems can include an AFE for measuring a bioelectric signal, an ADC for digitizing the measured bioelectric signal, an anti-aliasing filter, a controller for administrating the acquisition of the bioelectric signal, and downstream computational and analysis components that can operate upon the acquired bioelectric signals. The downstream computational component could be a machine intelligence inference generator that identifies a bioelectric signal associated with a biological occurrence and outputs a control signal in response. FIG. 1 includes a block diagram of three bioelectric signal acquisition systems 100, 110, and 120 that each exhibit these components in various configurations as will be described below.

The components listed in the prior paragraph can be used to simultaneously sample a plurality of bioelectric signals. For example, the AFE could take a single sample and generate a given voltage that represents a combination of a plurality of bioelectric signals which have combined to present that given voltage. The ADC could then simultaneously acquire that plurality of bioelectric signals by converting the given voltage into a digital value. As such, both the measurement and the acquisition of the bioelectric signal can be conducted simultaneously. This functionality enables numerous applications. For example, in the context of a display in a pair of augmented reality glasses, the system could detect eye movements, and output cursor movement control signals, while simultaneously detecting jaw clenches, and outputting cursor selection control signals. As another example, in the same context, two different biological signals could be acquired and combined for analysis to detect a single biological occurrence and thereby increase the accuracy of that detection.

In specific embodiments of the invention, the bioelectric signal acquisition systems disclosed herein can be embodied in various settings. The bioelectric signal acquisition systems could be part of an external health monitoring system incorporated into a piece of exercise equipment or a smart surface such as a sensor-enabled bathroom countertop. The bioelectric signal acquisition systems could be part of an internal health monitoring system such as an implanted sensor. The bioelectric signal acquisition systems could comprise a wearable device with integrated sensors. The wearable device could be a head-wearable device such as an earpiece (e.g., a wireless earbud), a pair of wireless earbuds, a pair of wired earbuds, a virtual reality headset, a pair of augmented reality glasses, a smart watch, a smart ring, other smart jewelry, any article of clothing with integrated sensors for measuring bioelectric signals, or any other wearable. FIG. 2 provides an illustration of various wearable devices that could be part of the bioelectric signal acquisition systems mentioned herein. FIG. 2 includes earpiece 200, smart watch 210, virtual reality headset 220, augmented reality glasses 230, wired earbuds 240, or wired Bluetooth earbuds 250. These specific settings are provided as examples only and should not be limited to the specific illustrations as the systems disclosed herein can be applied to a wide variety of devices.

Regardless of the setting of the bioelectric signal acquisition systems, all the elements of the systems as described above, such as those in FIG. 1, could be part of the mentioned setting or they could be distributed across various elements and in operative communication via a network connection. For example, an AFE and ADC could be on an earpiece while additional digital processing could be conducted by a user's smartphone that was in communication with the earpiece. As another example, an AFE and ADC could be on a smart surface while the further digital processing was conducted by a remote server in networked communication with the smart surface such that the bioelectric signals were acquired entirely by the wearable device, but the analysis and further downstream computations were conducted elsewhere.

Figure 3:
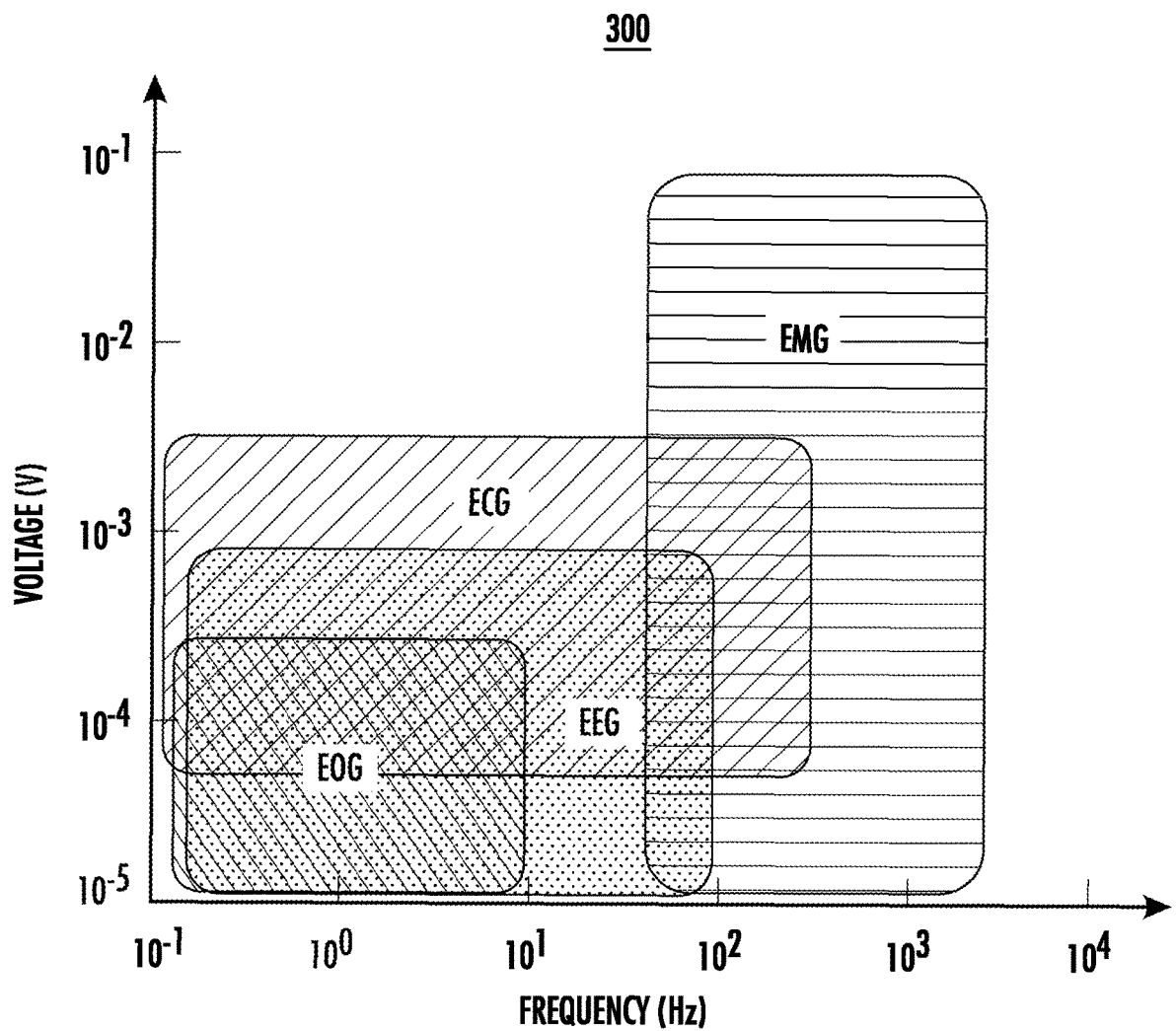
FIG. 3 illustrates a plot of the frequency and signal strength of various bioelectric signals that can be acquired simultaneously using bioelectric signal acquisition systems that are in accordance with specific embodiments of the inventions disclosed herein.

In specific embodiments of the invention, the bioelectric signal acquisition systems disclosed herein can be configured to detect various different bioelectric signals such as electroencephalograms (EEG) which are electrophysiological signals originating from brain activity, electrocardiograms (ECG) which are electrophysiological signals originating from heart activity, electromyogram (EMG) which are electrophysiological signals originating from muscular activity, electrooculography (EOG) which are electrophysiological signal originating from eyes movements and blinks, and other electrophysiological signals. FIG. 3 provides a chart 300 of the frequency range in Hertz (Hz) of the signals listed above plotted against the amplitude of these electrophysiological signals in volts. As illustrated, there are various portions of each type of signal along the frequency and voltage distributions which are unique to each signal. As such, the signals can be independently detected even when sampled simultaneously. Furthermore, only subsets of the illustrated bandwidths are relevant to detect a biological occurrence. For example, the "useful" EEG bandwidth is around 0.5 to 30 Hz and can be narrowed down further depending upon the type of brain activity studied. Accordingly, as used herein, the term "bioelectric signal" refers to a specific portion, in the frequency domain, of an electrophysiological electrical signal that can be used to detect a biological occurrence such as paying attention to a specific sound, blinking, moving an eyeball, a heart rate, etc.

Bioelectric signal acquisition systems in accordance with specific embodiments disclosed herein can include various types of AFEs. The systems disclosed herein could include AFEs for detecting any type of biological signal including sampling electric, thermal, or chemical inputs and converting any of those signals into an electronic signal for processing by an ADC. While examples involving detected electronic biological signals are used throughout this disclosure, specific embodiments disclosed herein are more widely applicable to biological signal acquisition systems used to detect any biological signal. In specific embodiments, the sampled biological signal will be electric. For example, a bioelectric signal acquisition system could include one or more electrodes for measuring a voltage. The one or more electrodes could include one or more measurement electrodes and one or more reference electrodes with the AFE configured to detect one or more voltages applied across the one or more measurement and reference electrodes. The measurement electrode could be part of a differential pair of measurement electrodes that each takes samples from which a common mode signal can be removed to distinguish noise from the desired signal. The three bioelectric signal acquisition systems 100, 110, and 120 in FIG. 1 each include a measurement electrode 101 and a reference electrode 102 which serve as at least part of the AFE of the bioelectric signal acquisition systems. The three bioelectric signal acquisition systems 100, 110, and 120 also each include an AFE block 108 which includes an amplifier 109 and a filter 106. The filter is described below. The amplifier can be used to enhance the detected signal for later processing. The AFE block 108 could include an integrated circuit coupled to the measurement electrode 101 and reference electrode 102. The AFE, including the aforementioned electrodes, could be on a wearable device that forms part of the signal acquisition system. For example, the measurement electrodes could be integrated with an earpiece. FIG. 2 provided an example of earpiece 200 having a reference electrode 201 and a measurement electrode 202 for detecting a bioelectric signal produced when a user clenches their jaw.

Bioelectric signal acquisition systems in accordance with specific embodiments disclosed herein can include various types of ADCs. The ADC can perform a discretization of a signal at a given sampling frequency. For example, with a sampling frequency of 250 Hz a discrete value of the signal is measured every 4 milliseconds. In specific embodiments of the inventions disclosed herein, the signal sampled by the ADC will be multiple bioelectric signals that are sampled simultaneously, and which are later distinguished and disaggregated based on their different frequencies using known digital filtering and signal manipulation techniques. The ADC will also perform a digitization of the signal according to the resolution of the ADC. For example, if the ADC has an input range of 2 volts and a resolution of 10 bits, every voltage measurement of the physical signal will be rounded to the closest multiple of 1.953 mV which is the full input range of 2 volts divided by 2 to the tenth power. The ADCs used in this disclosure can be any form of ADCs including successive approximation registers (SAR) ADCs, delta-sigma modulator ADCs, pipeline ADCs, and ADCs having any other ADC architecture. The bioelectric signal acquisition systems of FIG. 1 each include an ADC 103. The ADC is located between the electrodes and a digital processing block 104. The digital processing block will conduct various signal analysis techniques on the sampled signals such as disaggregating the signals based on their frequencies and analyzing the signals to determine what biological occurrence they may be associated with. The digital processing block can preprocess the signals and then provide them to a classifier to determine what bioelectric occurrence they are associated with. The processing block will operate on the digitized signals from the ADC which is why the ADC is located between the electrodes and the processing block.

Bioelectric signal acquisition systems in accordance with specific embodiments disclosed herein can include an anti-aliasing filter as will be described in more detail below. The anti-aliasing filter can include a low-pass filter, a high-pass filter, a band-stop filter, a band-pass filter, or a combination thereof. The anti-aliasing filter can include analog filters, digital filters, or a combination of both analog and digital filters. In specific embodiments of the invention, the anti-aliasing filter can be configured to create one or more frequency gaps between one or more bioelectric signals. The frequency gaps can be created by the filters attenuating in the frequency gap. The filters can attenuate both noise and signal within the frequency gap and as such the filter can define what frequency the bioelectric signals disclosed herein occupy as they are further manipulated by the system. The frequency gaps can be positioned such that they minimize or outright prevent the impact of sub-Nyquist induced aliasing on the sampled signals as will be described using the approaches disclosed below.

In specific embodiments of the inventions disclosed herein, the anti-aliasing filter can include an analog filter. The analog filter can conduct one or more of the low-pass filtering, the high-pass filtering, the band-pass filtering, and the band-stop filtering for a particular anti-aliasing filter architecture. The analog filter can be made of electronic components that act on the electrical signal before it gets sampled. For example, bioelectric signal acquisition systems 100, 110, and 120 each include an analog filter 106 which low-pass filters the signal before it is sampled by ADC 103. In bioelectric signal acquisition system 110, the analog filter 106 also conducts a band-stop filtering operation on the signals to attenuate in a frequency gap as will be described below. The analog filters can be passive (i.e., made of passive components such as resistors and capacitors) or active (i.e., using active components such as operational amplifiers). Passive filters may be less efficient than active filters such that they may not be good candidates for operating on signals with strong noise. Furthermore, specific passive filters can be space intensive such that there may not be room for passive filters on a small electronic device that incorporates the bioelectric signal acquisition systems disclosed herein. Specific passive filters may also deform a signal in an unwanted way such as by causing phase shifts in the signal. However, specific active filters may have superior performance to such passive filters, but they consume more power and may be more expensive in some situations.

In specific embodiments of the inventions disclosed herein, the anti-aliasing filter can include a digital filter. The digital filter can conduct one or more of low-pass, high-pass, band-pass, and band-stop filtering for a particular anti-aliasing filter architecture. For example, bioelectric signal acquisition systems 100 and 120 include a digital filter 105 which is instantiated by digital processing block 104 and filters the signals after they have been sampled by the ADC. In specific embodiments in which the anti-aliasing filter conducts both types of filtering, one type of filtering can be conducted by an analog filter and one can be conducted by a digital filter. In specific embodiments of the invention, such as those in accordance with bioelectric signal acquisition system 100, a filter such as analog filter 106 can conduct a low-pass filtering operation and a filter such as digital filter 105 can conduct a band-stop filtering operation. Specific embodiments disclosed herein require the use of accurate band-stop or band-pass filters such that the attenuation within or outside the cutoff frequencies is strong and no residual signal pollutes the aliases that will sit in the frequency gaps. Digital filtering can be used for this purpose.

In specific embodiments of the invention, such as those in accordance with bioelectric signal acquisition systems 100 and 110, the sub-Nyquist sampling described herein is conducted by a digital sampler 107. The digital sampler can be instantiated by digital processing block 104. Approaches that are in accordance with bioelectric signal acquisition systems 100 and 110 can include two different sampling frequencies with ADC 103 conducting an oversampling and digital sampler 107 conducting the sub-Nyquist sampling described herein.

Generally, while electrodes can provide robust measurements of bioelectric signal patterns associated with EEG, ECG, EMG and EOG readings, these signals are hard to use as control signals. For example, wearable device neural interfaces configured to capture a muscle movement may confuse a voluntary muscle movement (a control signal) with an unintentional or involuntary muscle movement when the user is in motion (a false signal or noise) or with any other type of electromagnetic noise (e.g., due to the power grid). This generally limits the practical application of neural interfaces to situations where the user is still, which is of limited practical utility. However, once the signal is measured it can be applied to a computational analysis system, such as those powered by machine intelligence approaches, that can distinguish a control signal from such false signals even when a user is on the move or engaging in the activities of daily life. Furthermore, if multiple readings from various bioelectric signals are combined to detect a given biological occurrence (e.g., both EMG and EOG for detecting a given eye movement) the accuracy of detecting the occurrence of that biological occurrence can increase dramatically. In light of the foregoing, techniques such as the approaches disclosed herein are particularly beneficial in that they decrease the computational complexity of the additional analysis required to evaluate the digital signals without a loss in fidelity to the original bioelectric signals. Furthermore, the techniques disclosed herein allow for the simultaneous acquisition of multiple signals which can decrease computational complexity and make highly useful information available for detecting a given biological occurrence with more than one type of signal.

Figure 4:
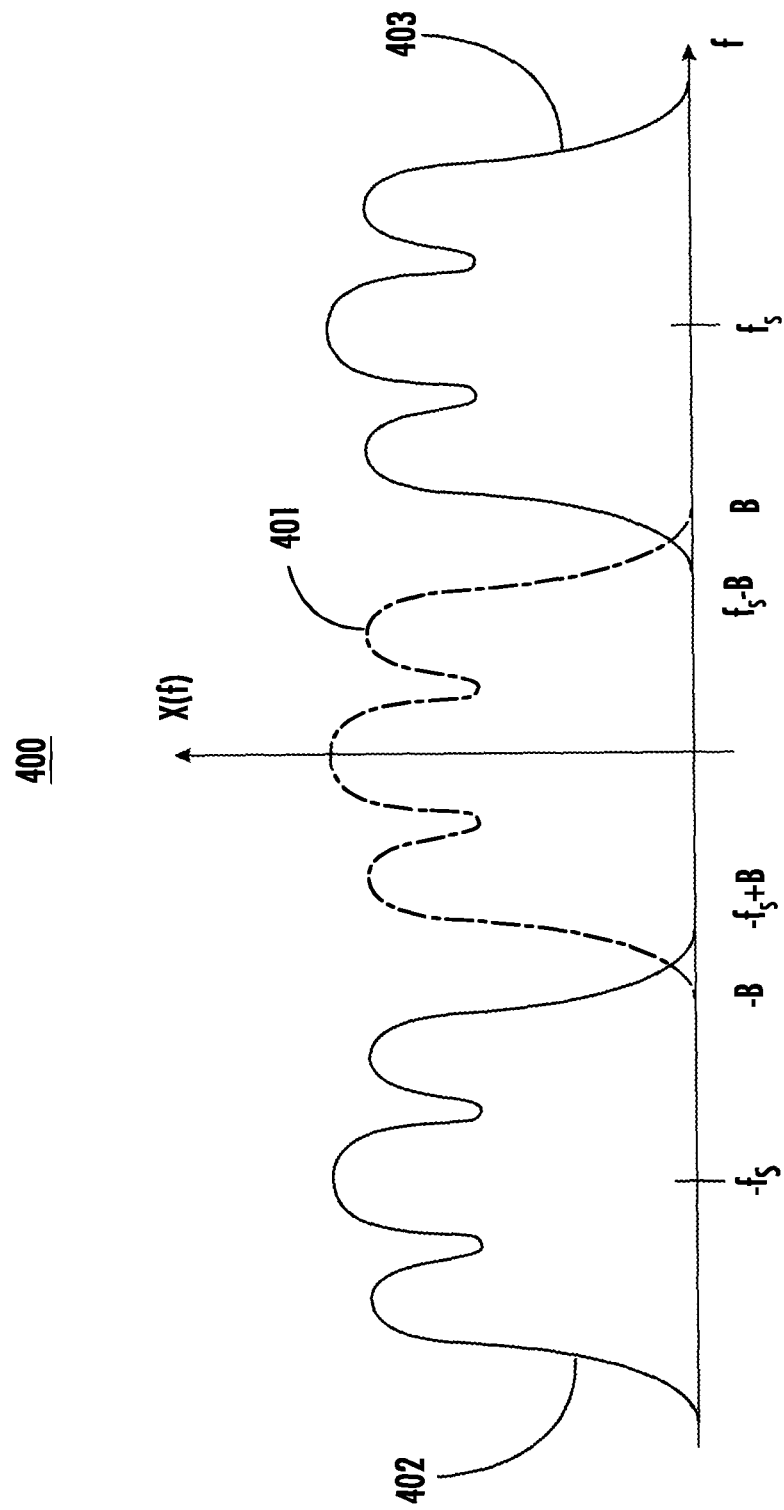
FIG. 4 illustrates a frequency plot of a bioelectric signal experiencing aliasing.

FIG. 4 illustrates a frequency plot 400 for purposes of explaining aliasing during sub-Nyquist sampling. Frequency plot 400 provides the amplitude X(f) of a signal 401 with a bandwidth B at a given frequency f along with the amplitude of two aliases 402 and 403 which result from the sampling of the signal at a sampling frequency fs. The graph illustrates how the spectrum of the signal is replicated at each multiple of fs with the replicated spectra being alias 402 and alias 403. In actuality, the replicated spectra would continue indefinitely in either direction along the frequency axis. In the illustrated case, since the signal has been sampled at a frequency fs which is below the Nyquist sampling rate of 2B, some overlap occurs, which results in the signal components proximate the highest frequency of B being polluted by the aliases. As a result, downstream computational systems will not be able to recover the original signal 401 if they are given the values of function X(f).

Figure 5:
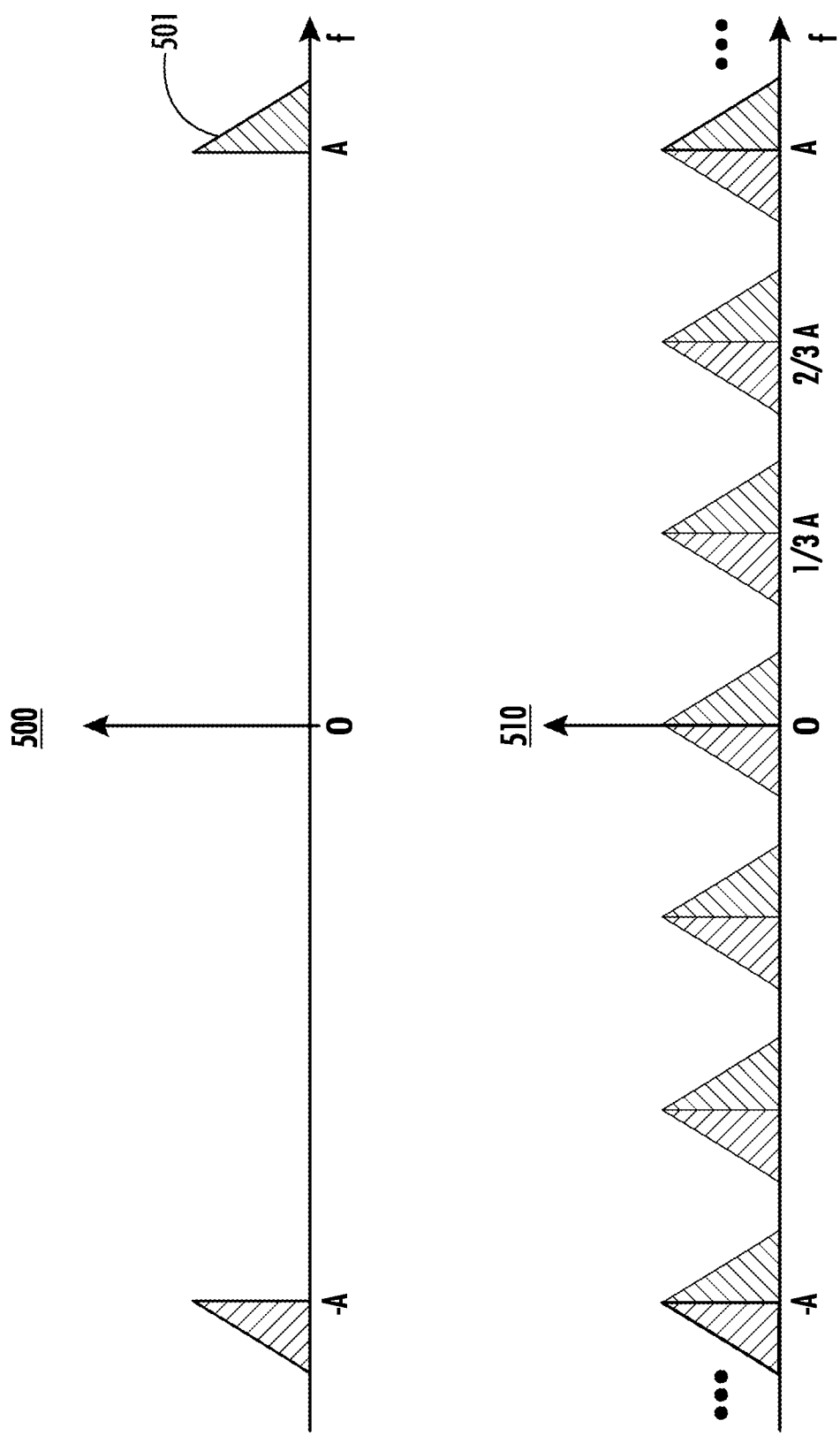
FIG. 5 illustrates frequency plots of a bioelectric signal being sampled using band-pass sampling.

FIG. 5 illustrates a frequency plot 500 of the amplitude of a signal 501 which results from a band-pass filtering operation in order to explain the principle of band-pass sampling. Signal 501 results from the band-pass filtering of a signal which attenuates in the frequencies below frequency A and above signal 501 as illustrated. FIG. 5 also illustrates a frequency plot 510 of the amplitude of the signal 501 after it has been sampled at a sub-Nyquist frequency of the signal 501. In this example, the sampling frequency is one-third of the lowest frequency A of the signal 501. As illustrated, although there are numerous aliases in frequency plot 510, they do not overlap signal 501, and signal 501 can be fully recovered from the sampled signal that is plotted on frequency plot 510. The illustrated approach can be referred to as band-pass sampling and involves the use of a band-pass filter to isolate the signal of interest (i.e., signal 501) followed by allowing aliasing by sampling at a sub-Nyquist frequency that is a factor of the lowest frequency of the signal of interest. For example, in the context of bioelectric signal sampling, an EMG bandwidth of interest from 80 to 120 Hz could be band-pass filtered and then sampled at a sub-Nyquist frequency of 80 Hz while still allowing for reconstruction of the EMG signal after sampling without any information loss.

In specific embodiments of the invention, band-pass sampling is not possible because simultaneous sampling of multiple bioelectric signals requires there to be multiple different signals at different bandwidths that are required to be sampled. As a result, it is not possible to only let a single signal pass through a band-pass filter and allow the remainder of the spectrum to be attenuated. For example, if on top of the EMG bandwidth mentioned in the prior paragraph, a system needed to analyze an EEG signal in a 1 to 30 Hz bandwidth, it would not be possible to use an analog band-pass filter to only preserve the 80 to 120 Hz bandwidth because the EEG signal would be fully attenuated and lost. Furthermore, even if both signals were preserved using filters that preserved both bands, a sampling frequency of 80 Hz would lead to an alias of the EMG signal overlapping the EEG bandwidth and causing information loss.

Figure 6:
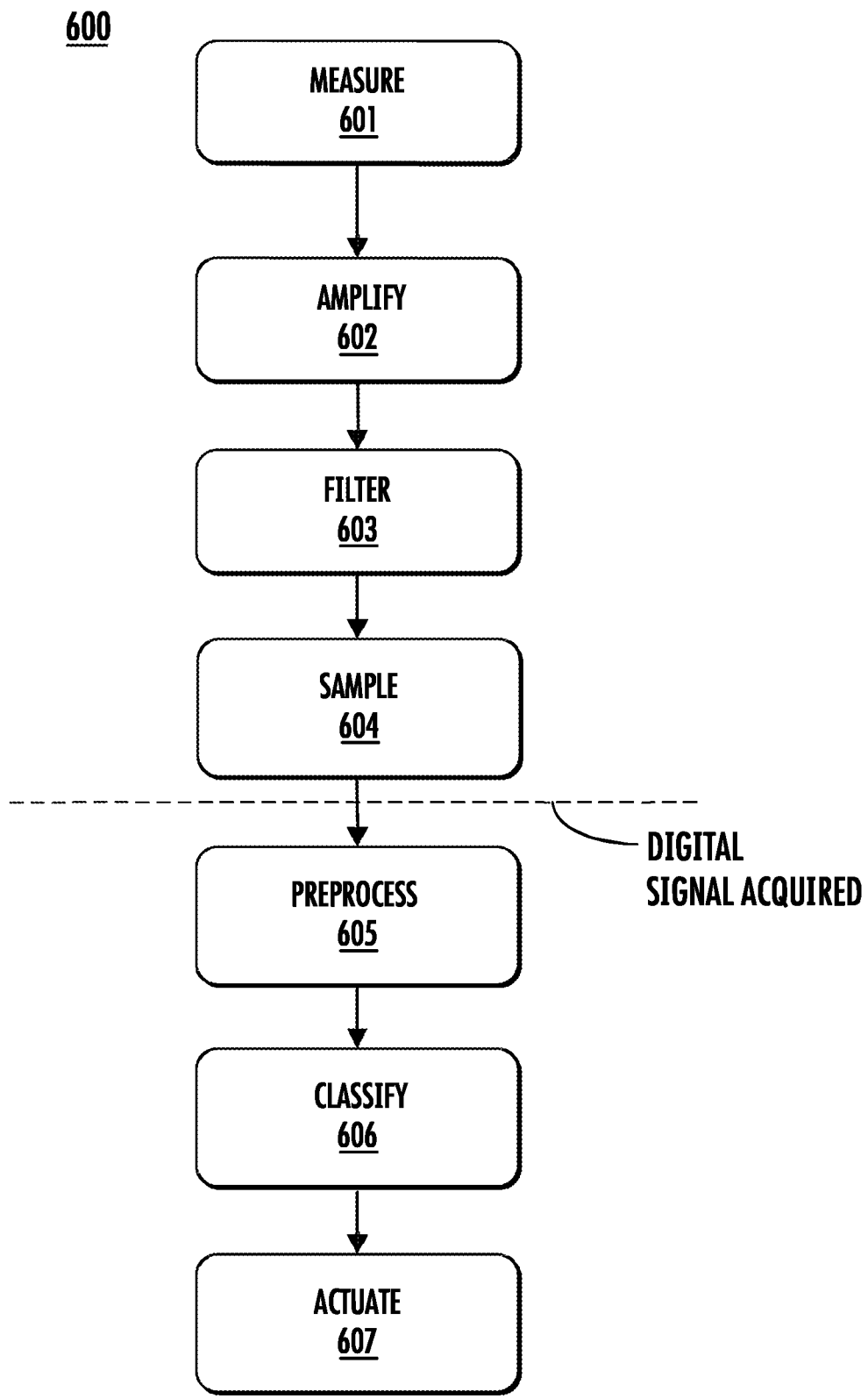
FIG. 6 illustrates a flow chart for a set of methods for acquiring a bioelectric signal in accordance with specific embodiments of the inventions disclosed herein.

FIG. 6 illustrates a flow chart 600 for a set of methods that can be used to simultaneously sample a plurality of bioelectric signals using a sub-Nyquist sampling rate without causing information loss. Specific embodiments of the illustrated methods can be conducted using systems such as those described with reference to FIG. 1. The first three steps of flow chart 600 are steps that are utilized to digitally acquire the signal. These include a step 601 of measuring a bioelectric signal, a step 602 of amplifying the measured signal, a step 603 of filtering (e.g., attenuating in a frequency gap), and a step 604 of sampling the bioelectric signal as measured in step 601. The final steps include additional computations that can be conducted on the signal once it is acquired. These include a step 605 of preprocessing the signal, a step 606 of classifying the signal to detect what biological occurrence it is associated with (e.g., recognizing a bioelectric signal as indicating a jaw clench), and a step 607 of actuating a control system based on the detecting of the biological signal as being associated with a biological occurrence (e.g., actuating a motor, sending a command to a peripheral using a controller, sending out a wireless signal from a transmitter using a controller, etc.). Step 606 can involve a complex computation conducted on a time series of values using a fuzzy logic analyzer or an artificial intelligence processing system such as an artificial neural network. Using specific embodiments of the invention disclosed herein for efficiently executing the first steps using a sub-Nyquist sampling rate, significant computational resources can be saved in the execution of steps 605 and 606 and the user experience provided by step 607 can be significantly enhanced.

In specific embodiments of the inventions disclosed herein, an analog filter or digital filter is configured to cutoff some frequencies to create a frequency gap and a sub-Nyquist sampling frequency is used to sample the resulting signal to allow for the simultaneous recording of a plurality of electrophysiological signals depending on their bandwidth of interest.

Flow chart 600 includes a step 601 of measuring, using an AFE (e.g., using a measurement electrode and a reference electrode), a first bioelectric signal and a second bioelectric signal simultaneously. This step can involve measuring a physiological bioelectric signal with an AFE to form a continuous time series of voltage measurements that are embodied in a potential or current in the AFE. In the case of two measurement electrodes, the measured signal could be a time varying potential difference between the two electrodes. The first bioelectric signal is within a first frequency band. The second bioelectric signal is within a second frequency band. The second frequency band is higher than the first frequency band. The first frequency band and the second frequency bands are separated by a frequency gap.

Figure 7:
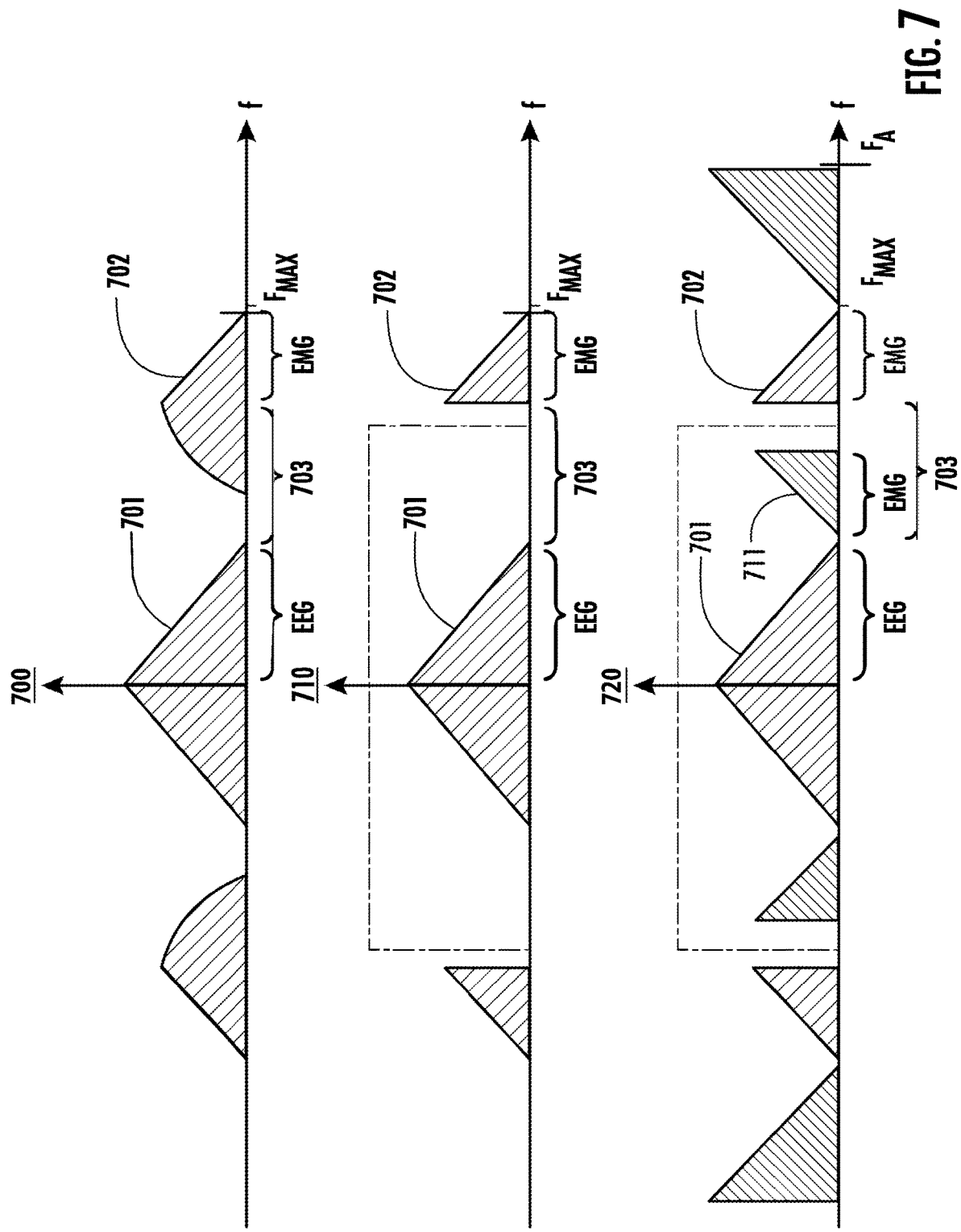
FIG. 7 illustrates frequency plots of two bioelectric signals being simultaneously sampled in accordance with specific embodiments of the inventions disclosed herein.

FIG. 7 illustrates an example of measured first and second bioelectric signals that exhibit the characteristics described in the prior paragraph. FIG. 7 includes a frequency plot 700 with a first bioelectric signal 701 and a second bioelectric signal 702. Frequency plot 700 includes an EEG signal 701 in a first frequency band marked EEG in the figure. Frequency plot 700 includes an EMG signal 702 in a second frequency band marked EMG in the figure. As illustrated, the second bioelectric signal, EMG signal 702, is part of a physiological bioelectric signal that spans a greater bandwidth than the second bioelectric signal itself. This physiological bioelectric signal includes EMG signal 702 and a separate portion which is not an EMG signal. As illustrated, the other portion of the physiological bioelectric signal is within frequency gap 703. Although it is simultaneously measured with second bioelectric signal 702, that alternative portion of the physiological bioelectric signal, which is not part of the EMG signal, will be filtered out, after being measured but before second bioelectric signal 702 is sampled, as will be described below with reference to step 603.

Flow chart 600 continues with a step 603 of filtering (e.g., attenuating in the frequency gap between the first frequency band and the second frequency band) using a filter. For example, the attenuating can be conducted to remove any signal or noise in the frequency band between the first bioelectric signal and the second bioelectric signal. As illustrated in frequency plot 710 in FIG. 7, this results in all signals and noise being removed in frequency gap 703. The filter can be a band-stop filter that filters out all power in the frequency band from the measured physiological signal. The filtering can be conducted using an analog filter that filters the signal prior to its conversion into a digital form by the ADC. In alternative approaches, the filtering can be conducted using a digital filter after the measured physiological signals have been digitized by an ADC. In specific embodiments, an ADC can sample the bioelectric signals at a sub-Nyquist frequency after the execution of step 603 as will be described below. For example, the ADC could sample the first and second bioelectric signals at a frequency less than twice $F_{MAX}$. In alternative specific embodiments, the ADC can sample the physiological signals at a frequency which is higher than the Nyquist frequency for the highest frequency bioelectric signal in the plurality of bioelectric signals that are being analyzed. As will be described below, the sampling frequency should also be a multiple of the sub-Nyquist sampling frequency. For example, the ADC could sample the signals in frequency plot 700 at a sampling rate that is higher than twice that of $F_{MAX}$. As a result, the bioelectric signals will all be digitized without information loss. Subsequently, a digital filter could attenuate the measured and digitized signals in the frequency gap and a digital sampler could then conduct the sub-Nyquist sampling mentioned herein.

In specific embodiments of the invention, a band-stop filter is used and tuned on top of alternative filters such as a band-pass filter or low-pass filter to prepare the bioelectric signals for sampling. The band-pass filter or low-pass filter could be an analog filter. In specific embodiments, the filter that attenuates in the frequency gap can be an analog cut-band filter. In specific embodiments of the inventions disclosed herein, the filter is combined with a low-pass filter for attenuating above the second frequency band. For example, a low-pass filter could attenuate any signal above $F_{MAX}$ in frequency plot 700. The low-pass filter could be an analog low-pass filter placed between the measurement electrodes and the ADC.

Specific embodiments of the inventions disclosed herein can continue with a step of sampling the plurality of measured bioelectric signals. The sampling can be conducted at a sub-Nyquist frequency of the highest frequency bioelectric signal in the plurality of measured bioelectric signals. For example, flow chart 600 can continue with a step 603 of sampling the first bioelectric signal and the second bioelectric signal. The sampling frequency can be less than two times $F_{MAX}$ such that aliasing occurs below $F_{MAX}$. However, by selecting the frequency gap created in step 603 and the sampling frequency used in step 603, there may be no overlap in the frequency domain between the aliases created by the sampling and the plurality of bioelectric signals.

In specific embodiments of the inventions disclosed herein, the sampling can be conducted using an ADC and by conducting a sampling at the sampling frequency. The sampling can be conducted on the first bioelectric signal and the second bioelectric signal as measured simultaneously by the measurement electrode and the reference electrode. As shown in frequency plot 720, the sampling frequency can be lower than the Nyquist frequency for the highest frequency signal in the plurality of bioelectric signals (e.g., lower than the Nyquist frequency for the second bioelectric signal 702). In the illustrated case, the sampling frequency is FA as marked on frequency plot 720 and an alias 711 of the second bioelectric signal 702, as caused by the sampling, is in the frequency gap 703. Furthermore, the alias 711 does not overlap the first frequency band EEG.

In specific embodiments of the invention, by choosing the sub-Nyquist sampling frequency and the one or more frequency gaps which will separate the bioelectric signals of interest, significant benefits can be realized by acquiring fewer samples of a plurality of bioelectric signals which can then be efficiently analyzed. The selection of the sub-Nyquist sampling frequency and the frequency gap can be selected based on various factors including the bandwidths of the bioelectrical signals of interest and their informational content, whether any overlap between the aliases and the signals or among the aliases is allowable, the number of bioelectrical signals of interest, the performance of available filters, and other factors. The selection process for the sampling frequency and frequency gap for various scenarios are described below. In specific embodiments of the invention the first, lower frequency, bioelectric signal is one of an ECG, EEG, and EOG signal, and the second, higher frequency, bioelectric signal is an EMG signal. While the examples below are generally limited to pairs of two types of bioelectric signals (e.g., EMG and EEG), any number of bioelectric signals, of any type, can be measured and acquired by adapting the teachings below.

Specific ranges that have been selected using the approaches disclosed below include the following. When dealing with the kinds of bioelectric signals discussed with reference to FIG. 3, a cutoff frequency of a low-pass filter can be between 95 and 160 Hz. In these applications, the frequency gap can be between 30 and 60 Hz. For example, the frequency gap can be 40 to 55 Hz. The sampling frequency can be below 160 Hz. In different applications, with a different frequency for the cutoff frequency of the low-pass filter, the frequency gap can be between 25 and 120 Hz. When the first bioelectric signal is an EEG and/or EOG signal and the first frequency band is between 0 and 30 Hz, and the second bioelectric signal is an EMG signal and the second frequency band is between 80 and 120 Hz, the frequency gap can be between 30 and 80 Hz and the sampling frequency can be between 150 and 160 Hz. When the first bioelectric signal is an EEG and/or EOG signal and the first frequency band is between 0 and 25 Hz, and the second bioelectric signal is an EMG signal and the second frequency band is between 62 and 98 Hz, the frequency gap can be between 25 and 62 Hz and the sampling frequency can be approximately 125 Hz. When the first bioelectric signal is an EEG and/or EOG signal and the first frequency band is between 0 and 25 Hz, and the second bioelectric signal is an EMG signal and the second frequency band is between 120 and 160 Hz, the frequency gap can be between 25 and 120 Hz, and the sampling frequency can be one of approximately 94 Hz, and between 185 and 320 Hz.

FIGS. 8-16 are similar graphs in which the x-axis is the sampling frequency selected for sampling the plurality of bioelectric signals and the y-axis shows the bandwidth of the plotted signals (i.e., the width of the plotted lines, when projected onto the y-axis, shows the spectrum occupied by the signals). The lines can therefore be referred to as the plotted bandwidths of the plotted signals. The plotted bandwidths show the aliases of the relative signals as aliased into the first Nyquist zone. When the plotted signals are horizontal, it means that there is no aliasing. For example, in FIG. 8 the plotted EEG spectrum is low frequency and as long as the sampling frequency is above the corresponding Nyquist rate there won't be any aliasing of the EEG spectrum. Since the x-axis plots begin around 25 Hz and the EEG spectrum is from around 5 Hz to 12 Hz in the illustrated case, the EEG bandwidth remains horizontal for the entire span of the chart.

Figure 8:
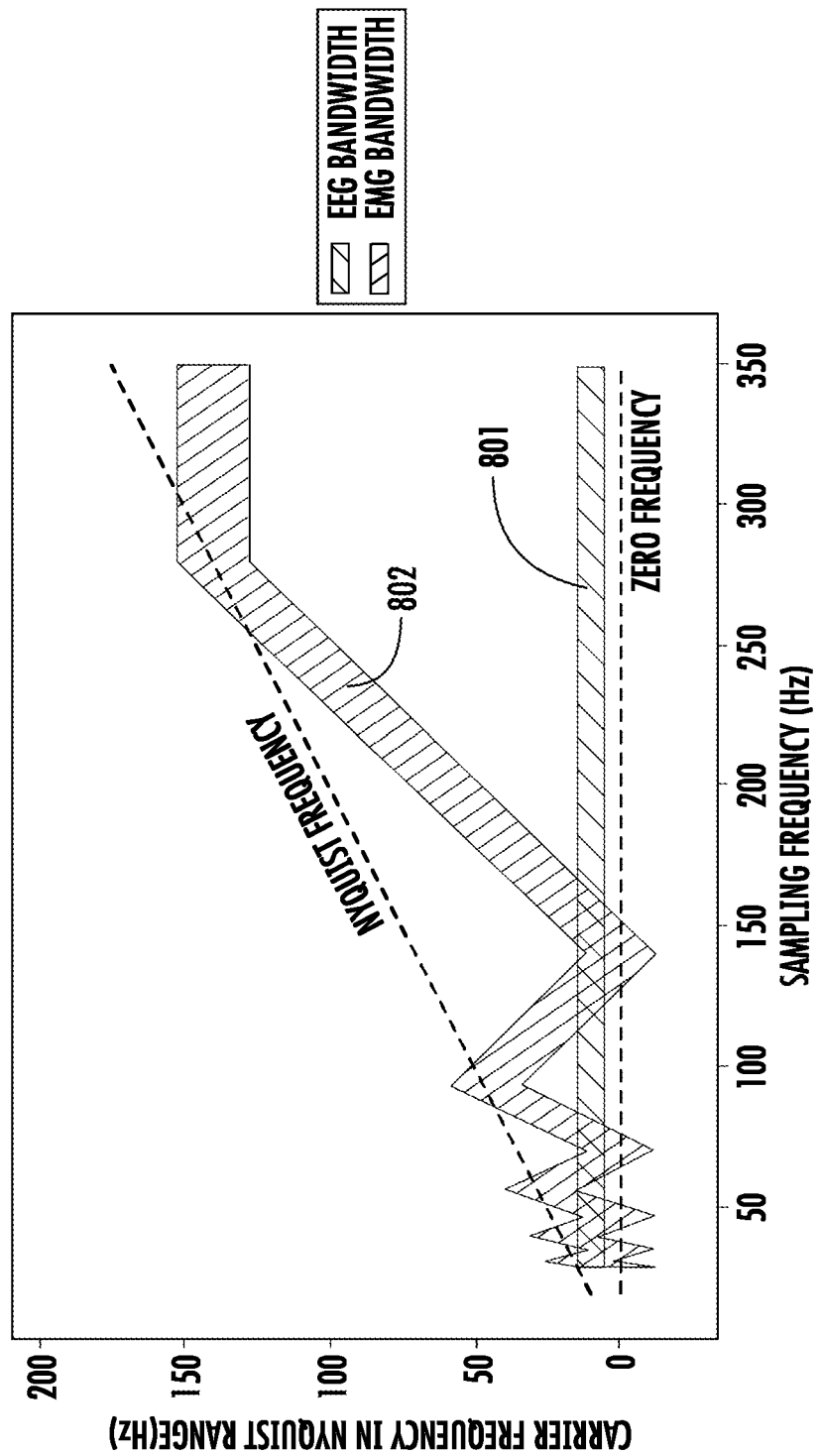
FIG. 8 illustrates a plot of the bandwidth of two bioelectric signals against a sampling frequency used to sample the two bioelectric signals in accordance with specific embodiments of the inventions disclosed herein.

In FIG. 8, two signals are plotted. Plot 801 is the EEG bandwidth. This can also be referred to as the first bioelectric signal. Plot 802 is the alias of the EMG signal projected into the first Nyquist zone of the combined first and second signals. This signal can also be referred to as the EMG alias or the second bioelectric signal alias. Plot 802 zig-zags back and forth because aliases can be projected forward and backwards through the Nyquist zone. Aliases can originate from either the spectrum in the positive frequencies, or its mirror spectrum in the negative frequencies. An alias of a signal in the positive frequency domain will increase in center frequency through the Nyquist zone as the sampling frequency increases. An alias of a signal in the negative frequency domain will decrease in center frequency through the Nyquist zone as the sampling frequency increases. Eventually, the plotted EMG alias stabilizes in a horizontal line. At this point, the sampling frequency exceeds twice the highest frequency component of the EMG signal and there is effectively no alias left in the first Nyquist zone.

To derive a general formula for where the alias appears and to produce plot 802 in FIG. 8, a projection of the center frequency of the EMG spectrum into the first Nyquist zone through aliasing is computed and then the full alias is deduced by using the EMG bandwidth $BW_{EMG}$. In the following equations $[F_{EEG_{min}}, F_{EEG_{max}}]$ is the interval of the EEG signal, $[F_{EMG_{min}}, F_{EMG_{max}}]$ is the interval of the EMG signal, $F_s$ is the sampling frequency, $F_{EEG_c}$ is the center frequency for the EEG signal, $F_{EMG_c}$ is the center frequency for EMG alias or EMG signal, $BW_{EEG}$ is the EEG bandwidth which is equal to $F_{EEG_{max}} - F_{EEG_{min}}$, and $BW_{EMG}$ is the EMG bandwidth which is equal to $F_{EMG_{max}} - F_{EMG_{min}}$. Accordingly, the equation for the projection of the EMG signal into the Nyquist zone follows the following equation which can be identified as equation 1 herein:

$$F_{EMG_{c\_proj}} = \begin{cases} F_{EMG_c} \% F_s & \text{if } \left\lfloor \dfrac{F_{EMG_c}}{F_s/2} \right\rfloor \text{ even} \\ F_s - (F_{EMG_c} \% F_s) & \text{if } \left\lfloor \dfrac{F_{EMG_c}}{F_s/2} \right\rfloor \text{ odd} \end{cases}$$

Where $F_{EMG_{c\_proj}}$ is the projection of $F_{EMG_c}$ in the first Nyquist zone, % is used to represent the modulo operator which gives the remainder of a division operation, and $\lfloor \_ \rfloor$ is used to represent the floor operator which rounds down to the nearest whole number. This equation is used to produce plot 802 in FIG. 8.

In specific embodiments of the invention, two types of sub-Nyquist sampling can be distinguished in the case of a plurality of bioelectric signals such as in the case of EEG and EMG signals. The two types are sub-Nyquist sampling with overlapping allowed and sub-Nyquist sampling without overlapping. Sub-Nyquist sampling without overlapping involves rendering the plurality of bioelectric signals (e.g., the EEG and EMG signals) in the first Nyquist zone without aliasing having any impact. As a result, the original signals can be restored from the sub-Nyquist sampled signal without needing the Nyquist criterion to be fulfilled. Frequency plot 720 is indicative of this occurrence as alias 711 is shown as not overlapping either signal 701 or 702. With reference to FIG. 8, the criterion for this occurrence are that plot 802 does not overlap plot 801 and the EMG spectra is contained within the first Nyquist zone such that the following condition is met $$\frac{BW_{EMG}}{2} < F_{EMG_{c\_proj}} < \frac{F_s - BW_{EMG}}{2}.$$

Figure 9:
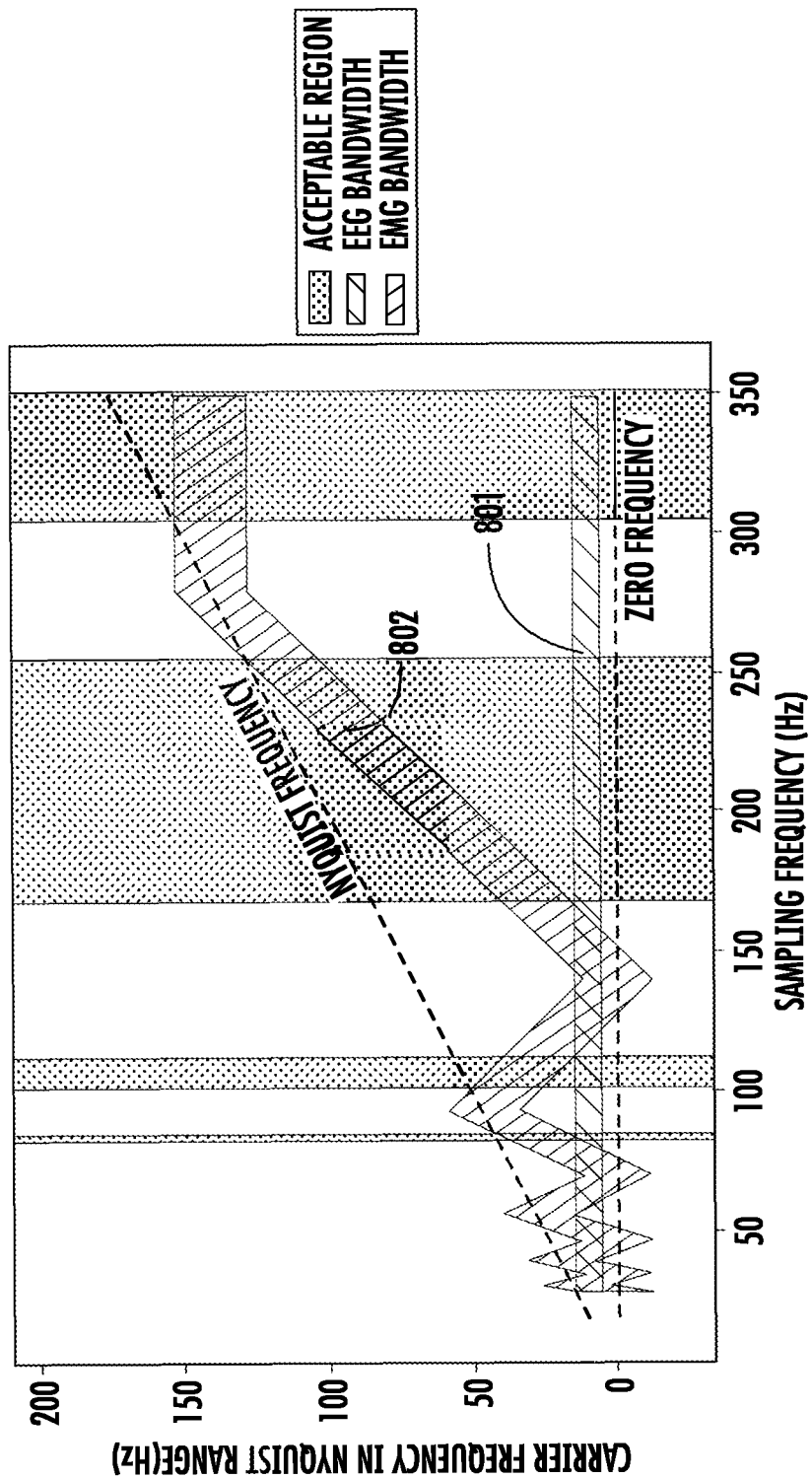
FIG. 9 illustrates the plot of FIG. 8 as annotated to show acceptable ranges for the sampling frequency some of which would result in sub-Nyquist sampling with no information loss in accordance with specific embodiments of the inventions disclosed herein.
Figure 10:
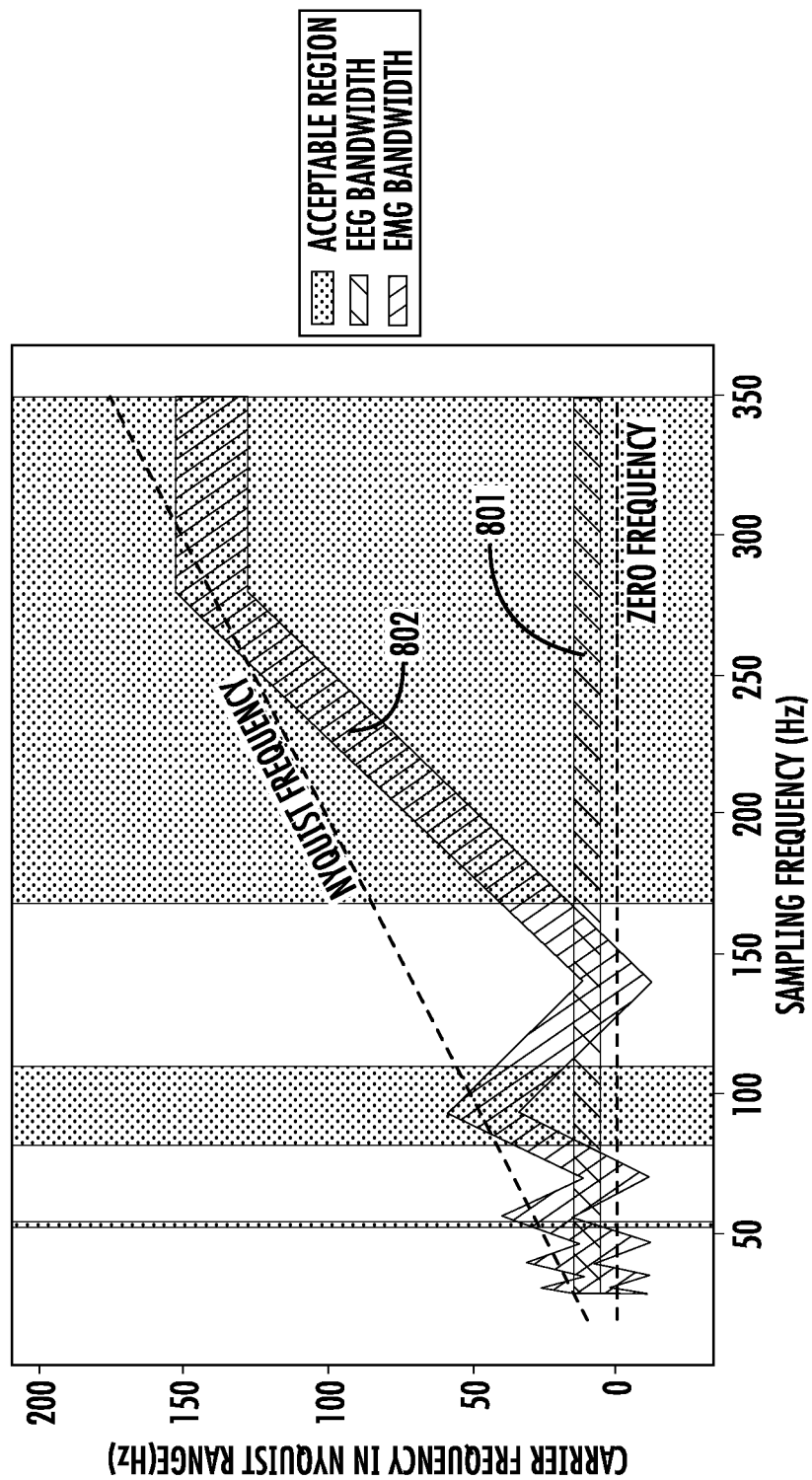
FIG. 10 illustrates the plot of FIG. 8 as annotated to show acceptable ranges for the sampling frequency some of which would result in sub-Nyquist sampling with acceptable overlap in accordance with specific embodiments of the inventions disclosed herein.

This means that the EEG and EMG spectra will both be present and untouched in the first Nyquist zone. The sampling frequency regions of plot 802 that meet this requirement are shown in FIG. 9 by shaded portions of the graph that are labeled acceptable regions. In these acceptable regions, the alias does not overlap with the first frequency band and is fully contained within the first Nyquist zone. As seen in FIG. 9, there are several distinct regions of acceptable values for the sampling frequency. These regions can be found non-graphically through the following criteria where the regions are identified by increasing numerals and represented by "n" in the following equations. This equation can be referred to as equation 2 herein.

$$\begin{cases} \dfrac{2}{n}[F_{EMG_{max}} + F_{EEG_{max}}] \leq F_s \leq \dfrac{2}{n-1} F_{EMG_{min}} & \text{if } n \text{ even} \\ \dfrac{2}{n} F_{EMG_{max}} \leq F_s \leq \dfrac{2}{n-1}[F_{EMG_{min}} - F_{EEG_{max}}] & \text{if } n \text{ odd} \end{cases}$$

$$\text{for } 1 \leq n \leq \left\lfloor \frac{F_{EMG_{max}}}{F_{EMG_{max}} - F_{EMG_{min}} + F_{EEG_{max}}} \right\rfloor$$

The case of n=1 is for the acceptable region set by the Nyquist criterion and the acceptable regions increase in number moving from right to left. If n=1 there is no upper limit to $F_s$ and the equation becomes $F_s \geq 2F_{EMG_{max}}$ which is the Nyquist criterion. As n gets higher, the sampling frequency gets lower.

Sub-Nyquist sampling with overlapping allowed involves rendering the plurality of bioelectric signals (e.g., the EEG and EMG signals) in the first Nyquist zone with aliases of the second frequency band partially overlapping with each other or with the signal. In the example of EEG and EMG signals, the signal in the EMG frequency band will overlap with its alias, or the EMG aliases will overlap with each other, but there will not be any interference with the EEG band. This would be equivalent to alias 711 partially overlapping with signal 702 in FIG. 7. The reason this is acceptable in specific embodiments is that the inventors have determined that the resulting acquired signal can still be used to detect a biological occurrence with sufficient accuracy even with a partial overlap of aliases of the same frequency band. For example, the signal used in step 604 in flow chart 600 can be a signal that has lost some information due to overlapping between aliases and the signal or among the aliases, but that information does not appear to have a major impact on the ability of the system to detect the underlying biological occurrence. The inventors have determined that for partial overlap of an EMG signal or other higher frequency bioelectric signal in the context of this disclosure, a partial overlap does not significantly reduce the performance of a machine learning algorithm such as a signature classifier used to discern a biological occurrence from an analysis of the acquired signal. When performing sub-Nyquist sampling with overlapping of a signal with its alias, or overlapping of its aliases with each other, allowed, the constraints can be relaxed. Graphically, the remaining constraint is for plots 801 and 802 to not overlap. These regions are marked as acceptable regions in FIG. 10. The constraints can also be described with reference to the following equation.

$$F_{EEG_{max}} < F_s - \left(F_{EMG_{c\_proj}} + \frac{BW_{EMG}}{2}\right)$$

However, since $F_{EMG_{c\_proj}}$ is in the first Nyquist zone:

$$F_{EMG_{c\_proj}} < \frac{F_s}{2}.$$

Thus, the equation becomes:

$$F_{EEG_{max}} < \frac{F_s - BW_{EMG}}{2}$$

This is equivalent to the first portion of equation 1 provided above. The acceptable regions for sub-Nyquist sampling with overlapping allowed can be found through the following equation which can be referred to herein as equation 3:

$$\frac{1}{n}[F_{EMG_{max}} + F_{EEG_{max}}] \leq F_s \leq \frac{2}{n-1}(F_{EMG_{min}} - F_{EEG_{max}})$$

$$\text{for } 1 \leq n \leq \left\lfloor \frac{F_{EMG_{max}} + F_{EEG_{max}}}{F_{EMG_{max}} - F_{EMG_{min}} + F_{EEG_{max}}} \right\rfloor$$

If n=1 there is no upper limit to $F_s$ and the equation becomes $F_s \geq F_{EMG_{max}} + F_{EEG_{max}}$.

Figure 11:
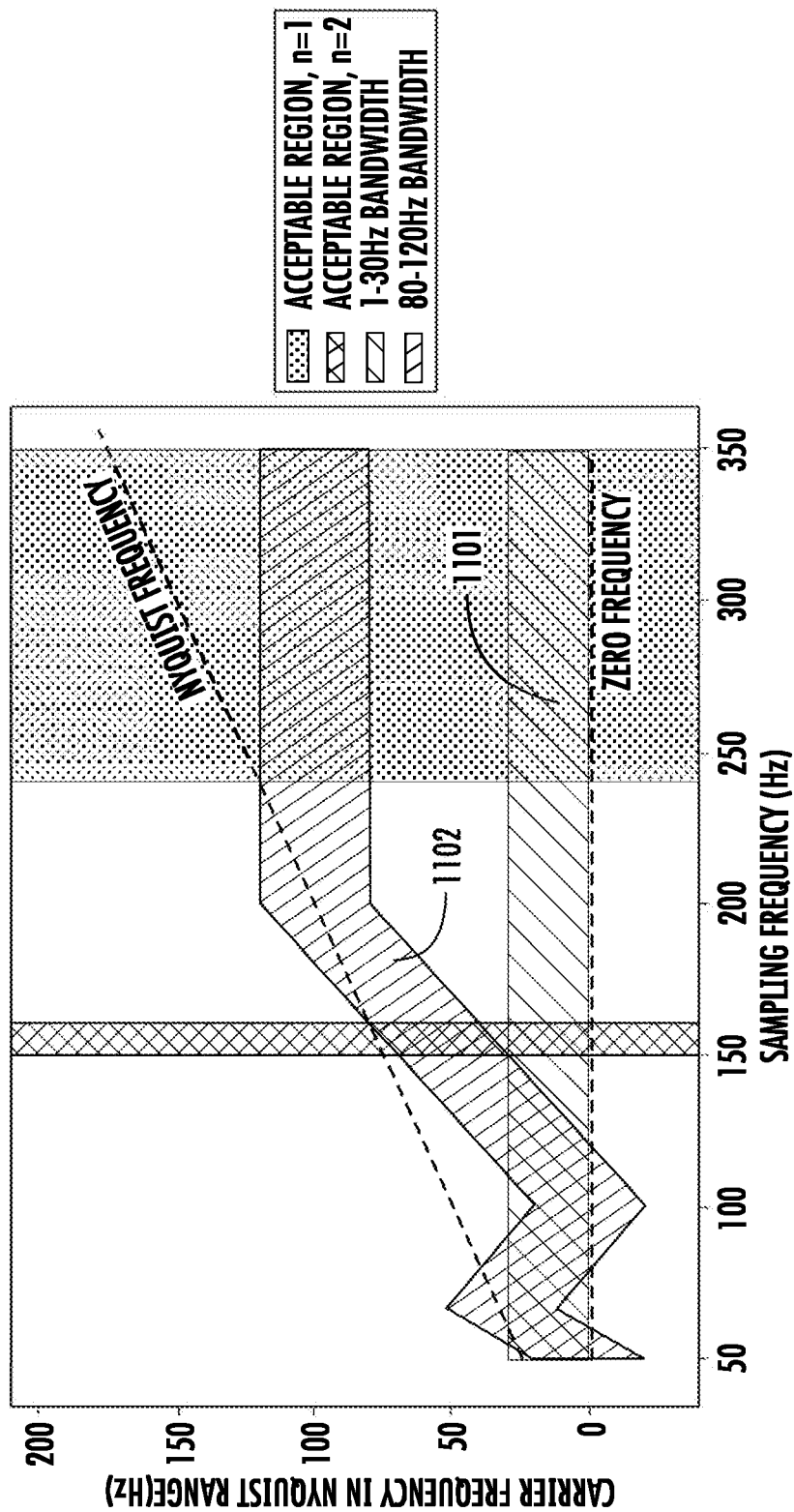
FIG. 11 illustrates a plot of the bandwidth of two bioelectric signals against a sampling frequency used to sample the two bioelectric signals annotated to show acceptable ranges for the sampling frequency some of which would result in sub-Nyquist sampling in accordance with specific embodiments of the inventions disclosed herein.

FIG. 11 illustrates a specific example of the sub-Nyquist sampling without overlapping approach with specific values for the bioelectric signals of interest. In the illustrated case, the "second bioelectric signal" is an EMG signal which lies between 80 and 120 Hz and the "first bioelectric signal" is an EEG or EOG signal that lies between 1 and 30 Hz. In this case, the frequency gap is 30 to 80 Hz and an analog filter is used to attenuate in that frequency band. When adding these values to equation 1 provided above, it can be seen that "n" must be less than or equal to 2 and $F_s \in [150,160] \cup [240,+\infty]$ Hz. This is also illustrated graphically in FIG. 11 with plot 1101 being the EEG or EOG bandwidth and plot 1102 being the EMG alias bandwidth. The figure also shows that in the acceptable region with n=2 the sampling frequency can be reduced from 240 to 150 Hz. Furthermore, in this example, if the numbers are applied to the equation 3 and overlapping of the EMG signal with its aliases or overlapping among its aliases can be allowed, it can be seen that there is no need to perform sub-Nyquist sampling with overlapping allowed. Allowing overlapping is not beneficial with this set of bioelectric signals because by replacing the values in equation 3 the same result is provided with $F_s \geq 150$ Hz and n=1. As such, in this case, it is better to perform sub-Nyquist sampling without overlapping as allowing overlapping in this case would not lead to a lower sampling frequency and allows for a full reconstruction of the signal if needed.

Figure 12:
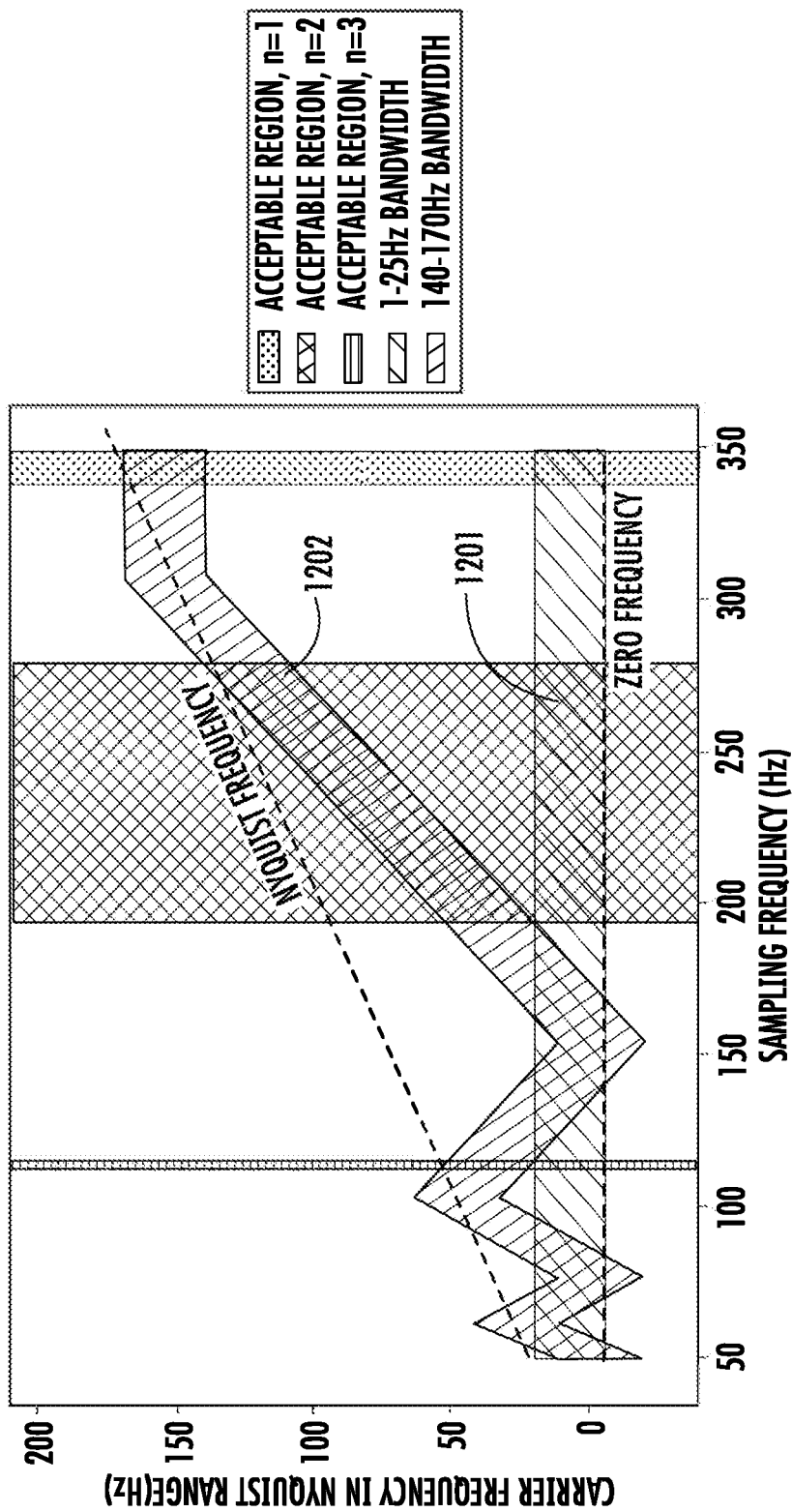
FIG. 12 illustrates a plot of the bandwidth of two bioelectric signals against a sampling frequency used to sample the two bioelectric signals annotated to show three acceptable ranges for the sampling frequency some of which would result in sub-Nyquist sampling with no information loss in accordance with specific embodiments of the inventions disclosed herein.

FIG. 12 illustrates a specific example of the sub-Nyquist sampling without overlapping with the addition of specific values for the bioelectric signals of interest. In the illustrated case, the "second bioelectric signal" is an EMG signal which lies between 140 and 170 Hz and the "first bioelectric signal" is either an EEG or EOG signal which lies between 1 and 25 Hz. When adding these values to equation 1, it can be seen that the possible values for "n" have increased in this case so that "n" can be equal to or less than 3 and $F_s \in [113.3,115] \cup [195,280] \cup [340,+\infty]$ Hz. The acceptable sampling frequencies are therefore over 340 Hz, between 195 and 280 Hz and between 113.3 and 115 Hz. This is also illustrated graphically in FIG. 12 with plot 1201 being the EEG or EOG bandwidth and plot 1202 being the EMG alias and signal bandwidth. These frequencies for the bioelectric signals allow for a reduction in the sampling frequency from 340 Hz (for traditional sampling which satisfies the Nyquist criterion) to around 114 Hz. In this case, the sampling frequency can be divided by 3, and the signal can be fully reconstructed, provided that the filters between 25 and 140 Hz are sufficiently steep.

Figure 13:
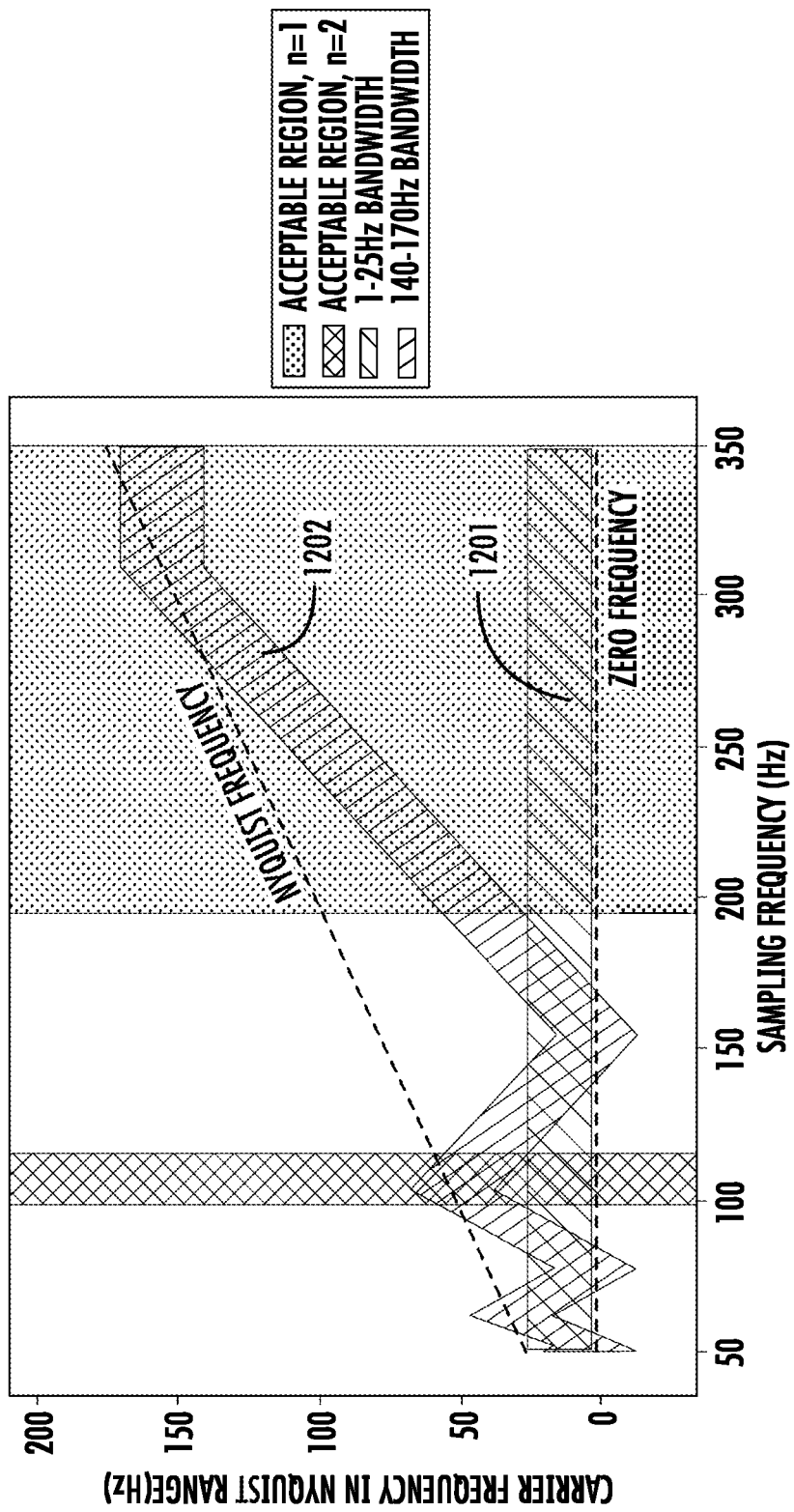
FIG. 13 illustrates the plot of FIG. 12 annotated to show acceptable ranges for the sampling frequency some of which would result in sub-Nyquist sampling with acceptable overlap in accordance with specific embodiments of the inventions disclosed herein.

FIG. 13 illustrates the same example as in FIG. 12, but with overlapping allowed. In this approach, the sampling frequency could be even further reduced to about 99 Hz as illustrated in FIG. 13 as it is acceptable for portions of plot 1202 to exceed the Nyquist frequency if overlapping is allowed. However, this reduction would only be a reduction of around 15 Hz and it would not be possible to fully reconstruct the original signal from the sub-Nyquist sampled one. As a result, keeping the sampling rate at around 114 Hz is preferable in specific applications in which loss of information is particularly problematic.

Figure 14:
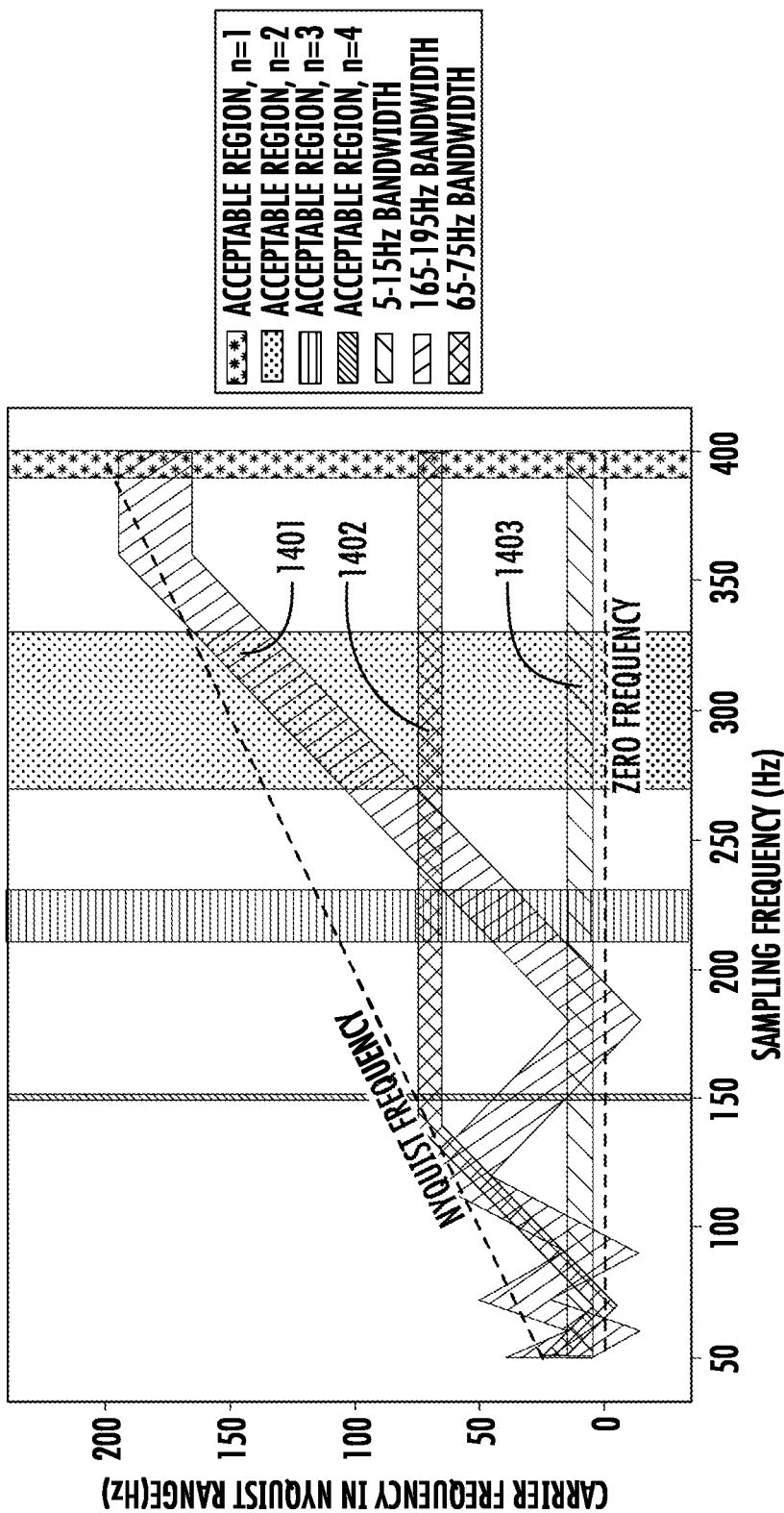
FIG. 14 illustrates a plot of the bandwidth of three bioelectric signals against a sampling frequency used to sample the three bioelectric signals annotated to show acceptable ranges for the sampling frequency some of which would result in sub-Nyquist sampling with no information loss in accordance with specific embodiments of the inventions disclosed herein.

FIG. 14 illustrates a specific example of the sub-Nyquist sampling where there are three different bandwidths of interest. The bandwidths of interest represent three different bioelectric signals that are to be measured and sampled simultaneously. In this example, the EMG signals now lie between 65 and 195 Hz. However, we suppose that the information between 75 and 165 Hz is useless in this case, and that the nature of the information contained below 75 Hz and above 165 Hz are unique signals. As a result, we will be dealing with two EMG frequency bands independently. These two bands are shown by plots 1401 and 1402 in FIG. 14. Additionally, the "first bioelectric signal" which in this case is an EEG or EOG signal is now restricted to 5 to 15 Hz. This band is shown by plot 1403 in FIG. 14. By replacing the values in equation 1, it is possible to determine that "n" must be less than or equal to 4 and the acceptable values for the sampling frequency are $F_s \in \{150\} \cup [210, 230] \cup [270,330] \cup [390, +\infty]$ Hz. These acceptable regions for the sampling frequency are shown in FIG. 14 for "n" going from 1 to 4. As illustrated, the approaches disclosed herein allow for a reduction in the sampling frequency from 390 Hz to 150 Hz which is a reduction by a factor of approximately 2.5.

Figure 15:
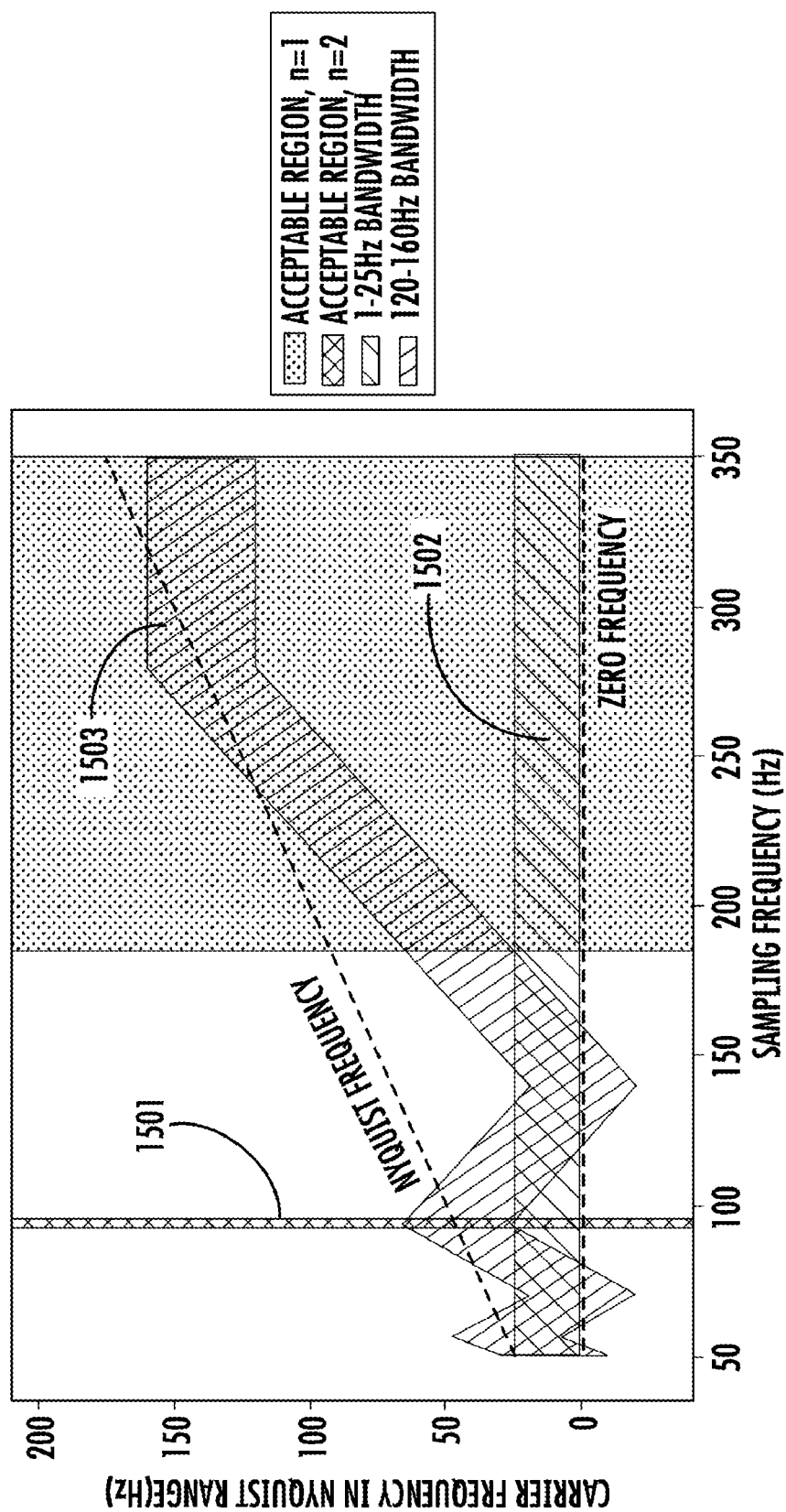
FIG. 15 illustrates a plot of the bandwidth of two bioelectric signals against a sampling frequency used to sample the two bioelectric signals annotated to show two acceptable ranges for the sampling frequency some of which would result in sub-Nyquist sampling with acceptable information loss in accordance with specific embodiments of the inventions disclosed herein.
Figure 16:
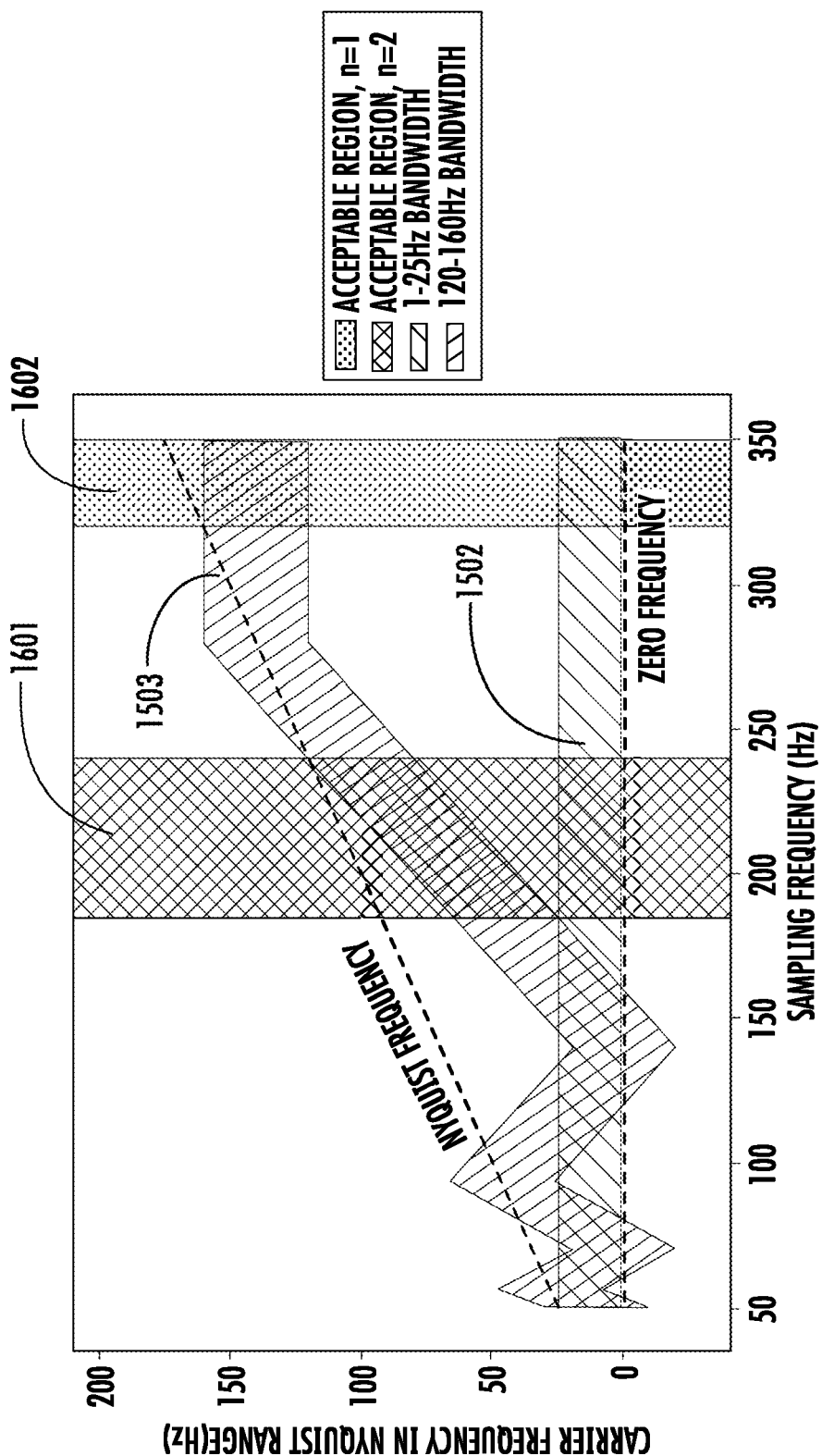
FIG. 16 illustrates the plot of FIG. 15 annotated to show two acceptable ranges for the sampling frequency some of which would result in sub-Nyquist sampling with no information loss in accordance with specific embodiments of the inventions disclosed herein.

In another example, the EMG frequencies of interest lie between 120 and 160 Hz while the EEG bandwidth is from 1 to 25 Hz. The equation used in this example is equation 3. Replacing the values of the equation with the ones stated above yields that "n" must be less than or equal to 2 and $F_s \in [93,95] \cup [185, +\infty]$ Hz. FIG. 15 illustrates the acceptable regions. In the n=2 acceptable region 1501, the EEG plot 1502 and EMG plot 1503 do not overlap. They carry different types of information and the frequential separation is preserved. However, the EMG plot 1503 will partially overlap with another EMG alias (as it crosses the Nyquist frequency limit represented with a dashed line). As a result, in the case of sub-Nyquist sampling with overlapping allowed, the sampling frequency can be reduced from 320 Hz to 93 Hz and is therefore divided by a factor of more than 3. However, the signal cannot be fully reconstructed (information loss because of the overlap). If the same numbers for the bioelectric signals were put into equation 2 for the scenario where overlapping is not allowed, the available values for the sampling frequency would be at least 185 Hz. This is shown graphically in FIG. 16 by a shift in the acceptable regions to region 1601 and region 1602. Indeed, replacing the variables from those equations yields "n" as equal to or less than 2 and $F_s \in [185,240] \cup [320, +\infty]$ Hz. As a result, if overlapping is not allowed to occur, the approaches disclosed herein lead to a reduction in the sampling frequency by a factor of less than 2.

In specific embodiments of the invention, the bioelectric signals are first sampled using a high sampling frequency that is equal to or exceeds the Nyquist rate and are then subjected to a sub-Nyquist sampling as described above. These processes would require two different samplers. For example, with the first sampler being part of the ADC that digitizes the signal and the second sampler being a digital sampler that operates in a digital processing block of the system. The oversampling frequency should be a multiple of the sub-Nyquist frequency. Accordingly, the approaches discussed above can be used to determine a sub-Nyquist frequency, and then the higher sampling frequency can be selected as a multiple of that sub-Nyquist frequency. The high frequency sampling can be referred to as oversampling the bioelectric signal. These approaches exhibit certain benefits in that there is no need for sharp analog filters for creating the one or more frequency gaps between the two or more bioelectric signals. The oversampling can be conducted when digitizing the signal and then a digital filter can be applied to create the frequency gaps.

In specific embodiments of the invention, digital filters can be applied to the sampled signals which are made up of coefficients by which to multiply the signal in order to draw out or suppress certain features. In the frequency domain, the filtering operation is a multiplication between the frequency representation of the signal and the filter. When transforming the signal back into the time domain, the filtering operation will have resulted in a convolution between the time domain signal and the impulse response of the filter.

Figure 17:
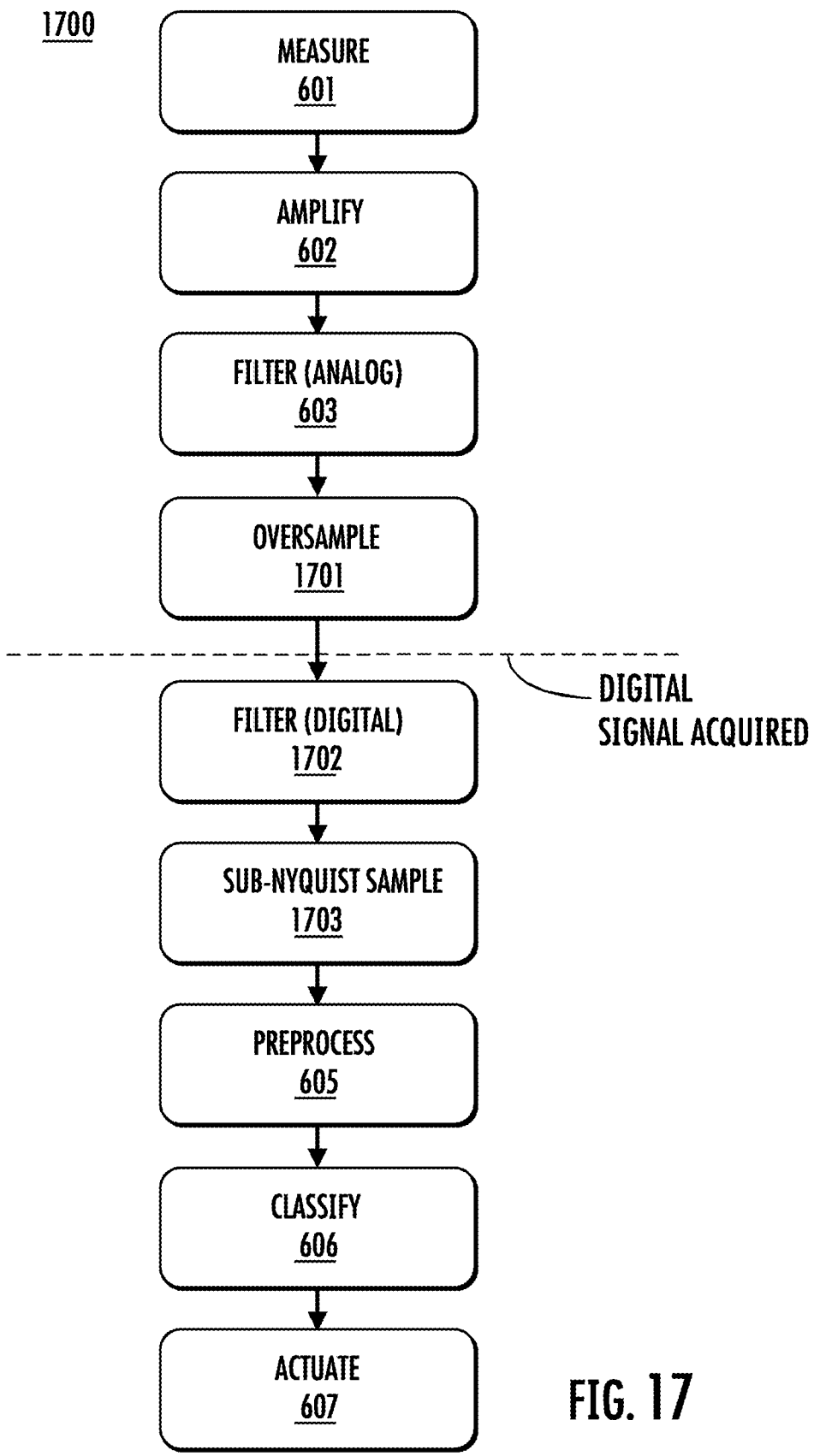
FIG. 17 illustrates a flow chart for a set of methods for simultaneously acquiring a plurality of bioelectric signals using oversampling and sub-Nyquist sampling in accordance with specific embodiments of the inventions disclosed herein.

FIG. 17 includes a flow chart 1700 for a method for sub-Nyquist sampling a signal using oversampling and sub-Nyquist sampling. In step 1701, the bioelectric signals are oversampled. The oversampling frequency respects two conditions: (1) the Nyquist criterion; and (2) it is a multiple of the sub-Nyquist frequency that will later be used in a step 1703. This second requirement is necessary so that there is no need to extrapolate the value of the data between two sampling points when conducting the sub-Nyquist sampling on the digitized signal. In other words, with this criterion met, the sub-Nyquist sampling process involves selecting specific values from the bioelectric signals as oversampled in step 1701. In specific embodiments, the chosen oversampling frequency is the smallest multiple of the selected sub-Nyquist sampling frequency which respects the Nyquist criterion. This frequency is chosen as benefits accrue to the minimization of both the oversampling frequency and the sub-Nyquist frequency. Step 1701 can be preceded by a measuring step as in step 601 of FIG. 6. The step can also be preceded by a step of filtering out high frequency components prior to the oversampling. This prior sampling step can be conducted using analog filters.

Flow chart 1700 continues with a step 1702 of filtering to create the frequency gaps mentioned in this disclosure between the two or more bioelectric signals. The step can be conducted similarly to step 603 in FIG. 6. In this step, the bioelectric signals can be digitally filtered to remove useless information and create the frequency gap for the controlled aliasing described in the approaches disclosed herein. The digital filters can be a low-pass filter and a band-pass filter in parallel or a low-pass filter and a band-stop filter in cascade. The digital filter can also be a band-stop filter operating on a signal that has already been subjected to a low-pass filtering operation such as via an analog filter.

Flow chart 1700 continues with a step 1703 of sub-Nyquist sampling the filtered bioelectric signals from step 1702. The step can be conducted similarly to step 603 in FIG. 6. The data can be sampled digitally by taking every N points of the filtered data where N is the number by which the sub-Nyquist sampling frequency is multiplied in order to get the oversampling frequency. The resulting signal is the simultaneously acquired multiple bioelectric signals. The signals can then be processed according to the same processes described previously with reference to steps 604 and 605 as if the signals had been subject to sub-Nyquist sampling after a frequency gap was formed in the signals using analog filters before they were initially sampled.

Figure 18:
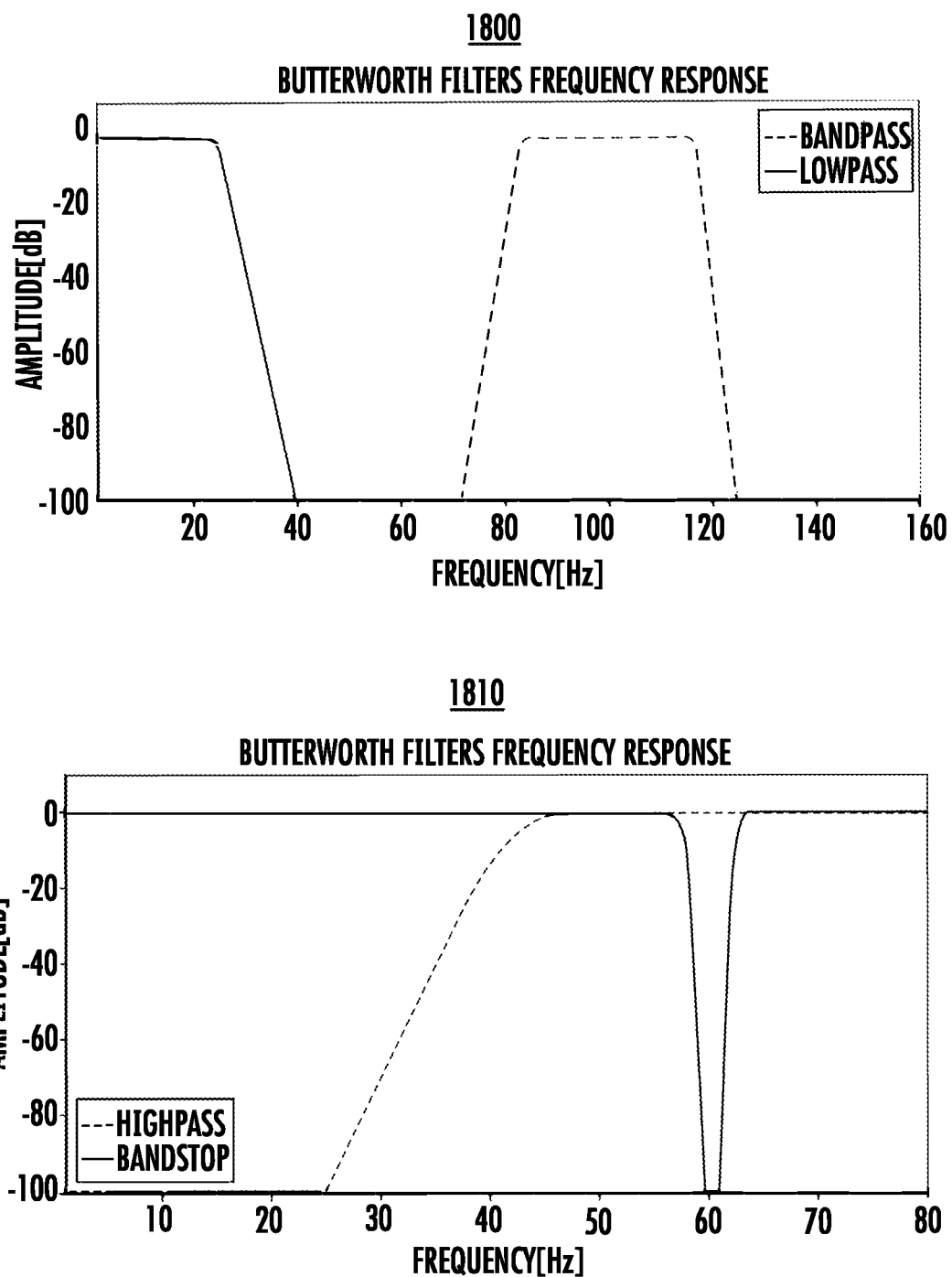
FIG. 18 illustrates the frequency responses of filters that can be used in accordance with specific embodiments of the inventions disclosed herein.

A specific implementation of the methods described with reference to flow chart 1700 can include EMG signals of interest that lie between 80 and 120 Hz and EEG/EOG signals of interest that lie between 1 and 30 Hz. The sub-Nyquist frequency in this case can be reduced to between 150 and 160 Hz such as 160 Hz. In accordance with this process, the signals can first be oversampled. In this situation, the Nyquist frequency is 240 Hz. The oversampling frequency is therefore 320 Hz because that is the smallest multiple of 160 Hz that exceeds 240 Hz. The data can then be digitally filtered to create the frequency gap used in the approaches disclosed herein. In this implementation, the filtering will attenuate between 30 and 80 Hz. Frequencies above 120 Hz can also be removed if they were not previously removed before the signal was originally oversampled. The filtering can be accomplished by a low-pass filter with a cutoff frequency of 25 Hz and a band-pass filter with cutoff frequencies at 82 and 117 Hz operating in parallel. These filters could have the frequency response illustrated in frequency plot 1800 in FIG. 18. The combined filters could be implemented as digital Butterworth filters. The data could then be sub-Nyquist sampled by taking every other data point in accordance with a sub-Nyquist sampling frequency of 160 Hz.

For an EMG application, the signals can then be filtered to only keep the aliased EMG information. Looking back to FIG. 11, for a sub-Nyquist sampling frequency of 160 Hz, the EMG data is aliased on the 40-80 Hz range. This means that in order to get the EMG information from the sub-Nyquist sampled signals, the following preprocessing needs to be applied. The signal needs to be applied to a high-pass filter with a cutoff frequency of 42 Hz and a band-stop filter with cutoff frequencies at 57.5 Hz and 62.5 Hz with a notch to remove the aliased 100 Hz harmonic of the EM line noise. The frequency response of these filters is shown in frequency plot 1810 in FIG. 18.

While the specification has been described in detail with respect to specific embodiments of the invention, it will be appreciated that those skilled in the art, upon attaining an understanding of the foregoing, may readily conceive of alterations to, variations of, and equivalents to these embodiments. Any of the method steps discussed above can be conducted by one or more processors operating with one or more computer-readable non-transitory media storing instructions for those method steps. The computer-readable media may be memory within a personal user device or a network accessible memory. Although examples in the disclosure where generally directed to the sampling of bioelectric signals, the same approaches could be utilized to the sampling of any biological signals, using any type of AFE, including auditory, visual, thermal, and chemical signal sampling which can be represented in the frequency domain such as by using a Fourier transform on a time series of the signal. These and other modifications and variations to the present invention may be practiced by those skilled in the art, without departing from the scope of the present invention, which is more particularly set forth in the appended claims.

What is claimed is:

1. A bioelectric signal acquisition system, comprising:
    a measurement electrode and a reference electrode, wherein the measurement electrode and the reference electrode are configured to measure a first bioelectric signal and a second bioelectric signal simultaneously, wherein: (i) the first bioelectric signal is within a first frequency band; (ii) the second bioelectric signal is within a second frequency band; (iii) the second frequency band is higher than the first frequency band; and (iv) the first frequency band and the second frequency band are separated by a frequency gap;
    a filter for attenuating in the frequency gap; and
    a sampler configured to sample, by conducting a sampling at a sampling frequency, the first bioelectric signal and the second bioelectric signal as measured simultaneously by the measurement electrode and the reference electrode;
    wherein: (i) the sampling frequency is lower than the Nyquist frequency for the second bioelectric signal; (ii) an alias of the second bioelectric signal caused by the sampling is in the frequency gap; and (iii) the alias does not overlap the first frequency band.

2. The bioelectric signal acquisition system of claim 1, wherein:
    the first bioelectric signal is one of an EOG, EEG, and ECG signal.

3. The bioelectric signal acquisition system of claim 1, wherein:
    the second bioelectric signal is an EMG signal.

4. The bioelectric signal acquisition system of claim 1, wherein:
    the alias is fully contained within the first Nyquist zone associated with the sampling frequency.

5. The bioelectric signal acquisition system of claim 1, wherein:
    at least two aliases of the second bioelectric signal caused by the sampling overlap in the first Nyquist zone associated with the sampling frequency.

6. The bioelectric signal acquisition system of claim 1, further comprising:
    an analog-to-digital converter configured to sample the first bioelectric signal and the second bioelectric signal as measured simultaneously by the measurement electrode and the reference electrode at a higher sampling frequency;
    wherein: (i) the sampler is a digital sampler; (ii) the higher sampling frequency is a multiple of the sampling frequency; (iii) the higher sampling frequency is higher than the Nyquist frequency for the second bioelectric signal.

7. The bioelectric signal acquisition system of claim 6, wherein the filter is one of:
    an analog cut-band filter;
    a digital band-pass filter and a digital low-pass filter; and
    a digital low-pass filter and a digital band-stop filter.

8. The bioelectric signal acquisition system of claim 1, wherein:
    the frequency gap is between 30 Hz and 60 Hz.

9. The bioelectric signal acquisition system of claim 1, wherein:
    the sampling frequency is below 160 Hz.

10. The bioelectric signal acquisition system of claim 1, wherein:
    the first bioelectric signal is an EEG signal, an EOG signal, or an EEG signal and EOG signal and the first frequency band is between 0 and 30 Hertz;
    the second bioelectric signal is an EMG signal and the second frequency band is between 80 and 120 Hertz;
    the frequency gap is between 30 and 80 Hertz; and
    the sampling frequency is between 150 and 160 Hertz.

11. The bioelectric signal acquisition system of claim 1, wherein:
    the first bioelectric signal is an EEG signal, an EOG signal, or an EEG signal and EOG signal and the first frequency band is between 0 and 25 Hertz;
    the second bioelectric signal is an EMG signal and the second frequency band is between 62 and 98 Hertz;
    the frequency gap is between 25 and 62 Hertz; and
    the sampling frequency is approximately 125 Hertz.

12. The bioelectric signal acquisition system of claim 1, wherein:
    the first bioelectric signal is an EEG signal, an EOG signal, or an EEG signal and EOG signal, and the first frequency band is between 0 and 25 Hertz;
    the second bioelectric signal is an EMG signal and the second frequency band is between 120 and 160 Hertz;
    the frequency gap is between 25 and 120 Hertz; and
    the sampling frequency is one of: (i) approximately 94 Hertz; and (ii) between 185 and 320 Hertz.

13. The bioelectric signal acquisition system of claim 1, further comprising:
    a low-pass filter for attenuating above the second frequency band;
    wherein the low-pass filter is an analog low-pass filter.

14. The bioelectric signal acquisition system of claim 13, wherein:
    the low-pass filter has a cutoff frequency; and
    the cutoff frequency of the low-pass filter is between 95 and 160 Hertz.

15. The bioelectric signal acquisition system of claim 1, wherein:
- a head-wearable device;
- wherein the measurement electrode, the reference electrode, the filter, and the sampler are all part of the head-wearable device.

16. A method, comprising:
- measuring, using a measurement electrode and a reference electrode, a first bioelectric signal and a second bioelectric signal simultaneously, wherein: (i) the first bioelectric signal is within a first frequency band; (ii) the second bioelectric signal is within a second frequency band; (iii) the second frequency band is higher than the first frequency band; and
- (iv) the first frequency band and the second frequency band are separated by a frequency gap;
- attenuating, using a filter, in the frequency gap; and
- sampling, using a sampler and by conducting a sampling at a sampling frequency, the first bioelectric signal and the second bioelectric signal as measured simultaneously by the measurement electrode and the reference electrode;
- wherein: (i) the sampling frequency is lower than the Nyquist frequency for the second bioelectric signal; (ii) an alias of the second bioelectric signal caused by the sampling is in the frequency gap; and (iii) the alias does not overlap the first frequency band.

17. The method of claim 16, wherein:
the first bioelectric signal is one of an EOG, EEG, and ECG signal.

18. The method of claim 16, wherein:
the second bioelectric signal is an EMG signal.

19. The method of claim 16, wherein:
the alias is fully contained within the first Nyquist zone associated with the sampling frequency.

20. The method of claim 16, wherein:
at least two aliases of the second bioelectric signal caused by the sampling overlap in the first Nyquist zone associated with the sampling frequency.

21. The method of claim 16, further comprising:
sampling, using an analog to digital converter, the first bioelectric signal and the second bioelectric signal, as measured simultaneously by the measurement electrode and the reference electrode, at a higher sampling frequency;
wherein: (i) the sampler is a digital sampler; (ii) the higher sampling frequency is a multiple of the sampling frequency; (iii) the higher sampling frequency is higher than the Nyquist frequency for the second bioelectric signal.

22. The method of claim 21, wherein the filter is one of:
an analog cut-band filter;
a digital band-pass filter and a digital low-pass filter; and
a digital low-pass filter and a digital band-stop filter.

23. The method of claim 16, wherein:
the frequency gap is between 30 Hz and 60 Hz.

24. The method of claim 16, wherein:
the sampling frequency is below 160 Hz.

25. The method of claim 16, wherein:
- the first bioelectric signal is an EEG signal, an EOG signal, or an EEG signal and EOG signal and the first frequency band is between 0 and 30 Hertz;
- the second bioelectric signal is an EMG signal and the second frequency band is between 80 and 120 Hertz;
- the frequency gap is between 30 and 80 Hertz; and
- the sampling frequency is between 150 and 160 Hertz.

26. The method of claim 16, wherein:
- the first bioelectric signal is an EEG signal, an EOG signal, or an EEG signal and EOG signal and the first frequency band is between 0 and 25 Hertz;
- the second bioelectric signal is an EMG signal and the second frequency band is between 62 and 98 Hertz;
- the frequency gap is between 25 and 62 Hertz; and
- the sampling frequency is approximately 125 Hertz.

27. The method of claim 16, wherein:
- the first bioelectric signal is an EEG signal, an EOG signal, or an EEG signal and EOG signal and the first frequency band is between 0 and 25 Hertz;
- the second bioelectric signal is an EMG signal and the second frequency band is between 120 and 160 Hertz;
- the frequency gap is between 25 and 120 Hertz; and
- the sampling frequency is one of: (i) approximately 94 Hertz; and (ii) between 185 and 320 Hertz.

28. The method of claim 16, further comprising:
attenuating, using a low-pass filter, above the second frequency band;
wherein the low-pass filter is an analog low-pass filter.

29. The method of claim 28, wherein:
the low-pass filter has a cutoff frequency; and
the cutoff frequency of the low-pass filter is between 95 and 160 Hertz.

30. One or more non-transitory computer-readable media storing instructions that, when executed by one or more processors of a bioelectric signal acquisition system, cause the bioelectric signal acquisition system to conduct a method comprising:
- measuring, using a measurement electrode and a reference electrode, a first bioelectric signal and a second bioelectric signal simultaneously, wherein: (i) the first bioelectric signal is within a first frequency band; (ii) the second bioelectric signal is within a second frequency band; (iii) the second frequency band is higher than the first frequency band; and (iv) the first frequency band and the second frequency band are separated by a frequency gap;
- attenuating, using a filter, in the frequency gap; and
- sampling, using an analog to digital converter and by conducting a sampling at a sampling frequency, the first bioelectric signal and the second bioelectric signal as measured simultaneously by the measurement electrode and the reference electrode;
- wherein: (i) the sampling frequency is lower than the Nyquist frequency for the second bioelectric signal; (ii) an alias of the second bioelectric signal caused by the sampling is in the frequency gap; and (iii) the alias does not overlap the first frequency band.

* * * * *